(12) United States Patent
Hepworth et al.

(10) Patent No.: US 11,213,635 B2
(45) Date of Patent: Jan. 4, 2022

(54) RECEPTACLE SECTION

(71) Applicant: BRITISH AMERICAN TOBACCO (INVESTMENTS) LIMITED, London (GB)

(72) Inventors: Richard Hepworth, Southampton (GB); Colin Dickens, London (GB)

(73) Assignee: British American Tobacco (Investments) Limited, London (GB)

( * ) Notice: Subject to any disclaimer, the term of this patent is extended or adjusted under 35 U.S.C. 154(b) by 241 days.

(21) Appl. No.: 16/333,568

(22) PCT Filed: Sep. 12, 2017

(86) PCT No.: PCT/EP2017/072813
§ 371 (c)(1),
(2) Date: Mar. 14, 2019

(87) PCT Pub. No.: WO2018/050612
PCT Pub. Date: Mar. 22, 2018

(65) Prior Publication Data
US 2019/0254345 A1    Aug. 22, 2019

(30) Foreign Application Priority Data
Sep. 14, 2016  (GB) .................................. 1615602

(51) Int. Cl.
*A61M 11/04*  (2006.01)
*A61M 15/06*  (2006.01)
(Continued)

(52) U.S. Cl.
CPC ........... *A61M 11/042* (2014.02); *A24F 40/40* (2020.01); *A24F 40/42* (2020.01); *A61M 15/06* (2013.01);
(Continued)

(58) Field of Classification Search
CPC ............... A61M 11/042; A61M 15/06; A61M 2205/3653; A61M 2205/8206; A24F 40/40; A24F 40/42
(Continued)

(56) References Cited

U.S. PATENT DOCUMENTS

| 4,338,931 A | 7/1982 | Cavazza |
| 6,382,465 B1 * | 5/2002 | Greiner-Perth ... A61M 15/0065 222/309 |

(Continued)

FOREIGN PATENT DOCUMENTS

| AR | 089648 A1 | 9/2014 |
| AR | 091949 A1 | 3/2015 |

(Continued)

OTHER PUBLICATIONS

International Preliminary Report on Patentability, Application No. PCT/EP2017/072813, dated Nov. 30, 2018, 9 pages.
(Continued)

*Primary Examiner* — Alexander Gilman
(74) *Attorney, Agent, or Firm* — Patterson Thuente Pedersen, P.A.

(57) ABSTRACT

A receptacle section for an aerosol provision article is described. The aerosol provision article is for generating a flow of aerosol in use. The receptacle section is arranged for having installed therein an activatable element for modifying, once activated, a property of the flow of aerosol. The receptacle section is arranged to apply, on installation of the activatable element in the receptacle section by a user, a force to the activatable element to activate the activatable element.

20 Claims, 10 Drawing Sheets

Figure 1:
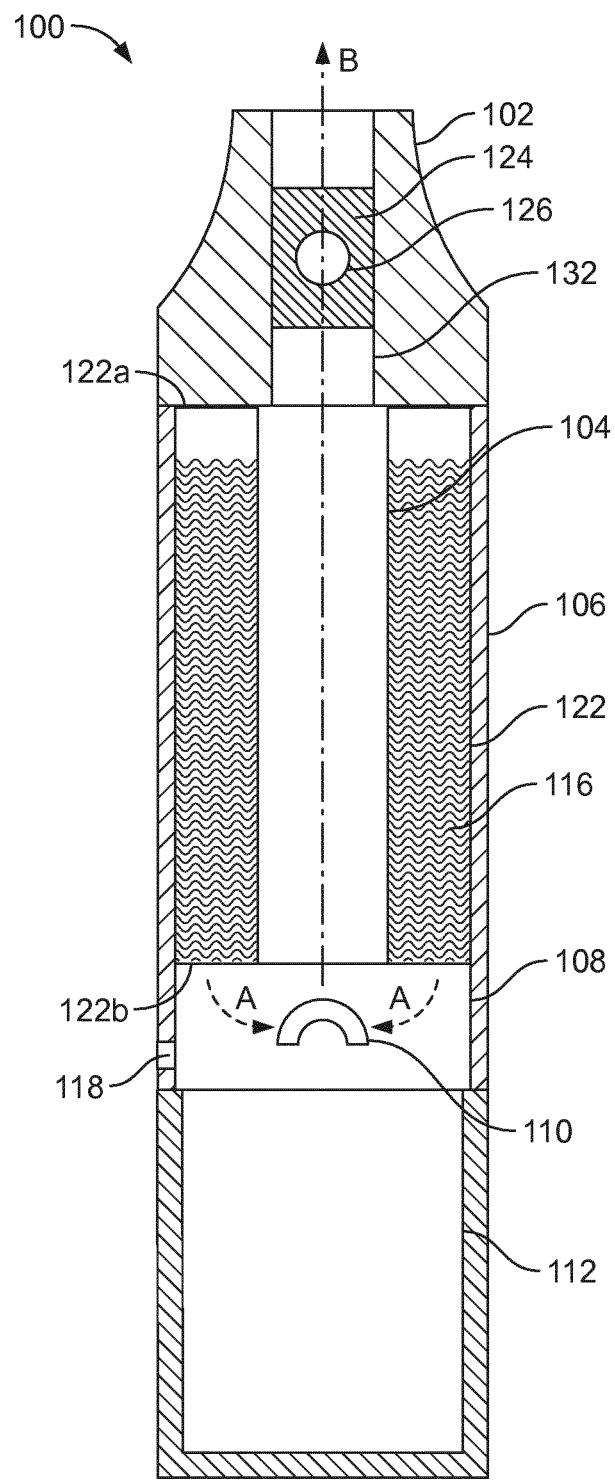

(51) Int. Cl.
*A24F 40/40* (2020.01)
*A24F 40/42* (2020.01)
*A24F 40/10* (2020.01)

(52) U.S. Cl.
CPC ...... *A24F 40/10* (2020.01); *A61M 2205/3653* (2013.01); *A61M 2205/8206* (2013.01)

(58) Field of Classification Search
USPC .......................................................... 131/329
See application file for complete search history.

(56) References Cited

U.S. PATENT DOCUMENTS

| | | | |
|---|---|---|---|
| 6,606,992 B1 | 8/2003 | Schuler et al. | |
| 6,705,313 B2 * | 3/2004 | Niccolai | A61M 15/0028 128/203.15 |
| 6,708,846 B1 * | 3/2004 | Fuchs | A61M 11/06 222/82 |
| 8,377,009 B2 * | 2/2013 | Sullivan | A61M 11/06 604/200 |
| 8,997,753 B2 | 4/2015 | Li et al. | |
| 8,997,754 B2 | 4/2015 | Tucker et al. | |
| 9,004,073 B2 | 4/2015 | Tucker et al. | |
| 9,247,773 B2 | 2/2016 | Memari et al. | |
| 9,282,772 B2 | 3/2016 | Tucker et al. | |
| 9,693,587 B2 * | 7/2017 | Plojoux | A61M 15/06 |
| 10,010,687 B2 | 7/2018 | Von Schuckmann | |
| 10,426,199 B2 * | 10/2019 | Turner | A61M 15/06 |
| 10,470,491 B2 | 11/2019 | Sutton et al. | |
| 10,492,526 B2 | 12/2019 | Sampson et al. | |
| 10,758,686 B2 | 9/2020 | Reevell | |
| 2005/0000518 A1 * | 1/2005 | Dunkley | A61M 15/0028 128/203.21 |
| 2005/0016533 A1 * | 1/2005 | Schuler | A61M 15/0093 128/203.15 |
| 2005/0022813 A1 * | 2/2005 | Alston | A61M 15/0028 128/203.21 |
| 2005/0048003 A1 * | 3/2005 | Ohki | A61M 15/0033 424/46 |
| 2005/0056280 A1 * | 3/2005 | Alston | A61M 15/0031 128/203.21 |
| 2005/0081852 A1 * | 4/2005 | Rangachari | A61M 15/0028 128/203.21 |
| 2005/0150492 A1 * | 7/2005 | Dunkley | A61M 15/0028 128/203.21 |
| 2007/0012327 A1 | 1/2007 | Karles et al. | |
| 2013/0042865 A1 | 2/2013 | Monsees et al. | |
| 2013/0068081 A1 | 3/2013 | Kronberg et al. | |
| 2013/0192615 A1 | 8/2013 | Tucker et al. | |
| 2013/0192616 A1 | 8/2013 | Tucker et al. | |
| 2013/0192619 A1 | 8/2013 | Tucker et al. | |
| 2013/0192620 A1 | 8/2013 | Tucker et al. | |
| 2013/0192621 A1 | 8/2013 | Li et al. | |
| 2013/0192622 A1 | 8/2013 | Tucker et al. | |
| 2013/0192623 A1 | 8/2013 | Tucker et al. | |
| 2013/0298905 A1 | 11/2013 | Levin et al. | |
| 2013/0312742 A1 | 11/2013 | Monsees et al. | |
| 2014/0202479 A1 | 7/2014 | Nicholls et al. | |
| 2015/0027469 A1 | 1/2015 | Tucker et al. | |
| 2015/0027477 A1 | 1/2015 | Yoshino et al. | |
| 2015/0245654 A1 | 9/2015 | Memari et al. | |
| 2015/0245655 A1 | 9/2015 | Memari et al. | |
| 2015/0245656 A1 | 9/2015 | Memari et al. | |
| 2015/0245657 A1 | 9/2015 | Memari et al. | |
| 2015/0245662 A1 | 9/2015 | Memari et al. | |
| 2015/0245663 A1 | 9/2015 | Memari et al. | |
| 2015/0245664 A1 | 9/2015 | Memari et al. | |
| 2015/0245665 A1 | 9/2015 | Memari et al. | |
| 2015/0245666 A1 | 9/2015 | Memari et al. | |
| 2015/0245667 A1 | 9/2015 | Memari et al. | |
| 2015/0245668 A1 | 9/2015 | Memari et al. | |
| 2015/0359266 A1 | 12/2015 | Memari et al. | |
| 2015/0374035 A1 | 12/2015 | Sanchez et al. | |
| 2016/0007648 A1 | 1/2016 | Sutton et al. | |
| 2017/0347706 A1 | 12/2017 | Aoun et al. | |
| 2018/0027882 A1 | 2/2018 | Hepworth et al. | |
| 2018/0279678 A1 | 10/2018 | Hepworth et al. | |
| 2018/0360122 A1 | 12/2018 | Aoun et al. | |
| 2019/0098930 A1 | 4/2019 | Fallon et al. | |
| 2019/0125988 A1 | 5/2019 | Trzecieski | |
| 2019/0230990 A1 | 8/2019 | Hepworth | |
| 2019/0254343 A1 | 8/2019 | Hepworth et al. | |
| 2019/0254344 A1 | 8/2019 | Hepworth et al. | |
| 2020/0060333 A1 | 2/2020 | Sutton et al. | |

FOREIGN PATENT DOCUMENTS

| | | |
|---|---|---|
| AU | 2013214984 A1 | 8/2014 |
| AU | 2013214987 A1 | 8/2014 |
| AU | 2013214991 A1 | 8/2014 |
| AU | 2013214993 A1 | 8/2014 |
| AU | 2013214994 A1 | 8/2014 |
| AU | 2013214997 A1 | 8/2014 |
| AU | 2013214998 A1 | 8/2014 |
| CA | 2845090 A1 | 2/2013 |
| CA | 2862105 A1 | 8/2013 |
| CA | 2862294 A1 | 8/2013 |
| CA | 2863185 A1 | 8/2013 |
| CA | 2863189 A1 | 8/2013 |
| CA | 2867620 A1 | 8/2013 |
| CA | 2867624 A1 | 8/2013 |
| CA | 2868313 A1 | 8/2013 |
| CN | 2760984 Y | 3/2006 |
| CN | 104219973 A | 12/2014 |
| CN | 104244749 A | 12/2014 |
| CN | 104244750 A | 12/2014 |
| CN | 104284606 A | 1/2015 |
| CN | 104302197 A | 1/2015 |
| CN | 104394722 A | 3/2015 |
| CN | 204275207 U | 4/2015 |
| CN | 104661544 A | 5/2015 |
| CN | 204560971 | 8/2015 |
| CN | 104968225 A | 10/2015 |
| EA | 201490448 A1 | 12/2014 |
| EP | 1555899 B1 | 12/2006 |
| EP | 2083643 B1 | 8/2009 |
| EP | 2723429 A1 | 4/2014 |
| EP | 2727619 A2 | 5/2014 |
| EP | 2740506 A1 | 6/2014 |
| EP | 2740507 A1 | 6/2014 |
| EP | 2740508 A1 | 6/2014 |
| EP | 2727619 A3 | 7/2014 |
| EP | 2756859 A1 | 7/2014 |
| EP | 2756860 A1 | 7/2014 |
| EP | 2809180 A1 | 12/2014 |
| EP | 2809182 A2 | 12/2014 |
| EP | 2809183 A1 | 12/2014 |
| EP | 2809184 A1 | 12/2014 |
| EP | 2809185 A1 | 12/2014 |
| EP | 2809186 A1 | 12/2014 |
| EP | 2809187 A1 | 12/2014 |
| EP | 2723429 A4 | 4/2015 |
| EP | 2809180 A4 | 7/2015 |
| EP | 2809184 A4 | 7/2015 |
| EP | 2809187 A4 | 7/2015 |
| EP | 2809182 A4 | 8/2015 |
| EP | 2809183 A4 | 8/2015 |
| EP | 2809185 A4 | 8/2015 |
| EP | 2809186 A4 | 9/2015 |
| EP | 2948006 A1 | 12/2015 |
| EP | 2964038 A1 | 1/2016 |
| EP | 2975956 A1 | 1/2016 |
| EP | 3039972 A1 | 7/2016 |
| GB | 201413018 | 9/2014 |
| GB | 201413019 | 9/2014 |
| GB | 201413021 | 9/2014 |
| GB | 201413025 | 9/2014 |
| GB | 201413027 | 9/2014 |
| GB | 201413028 | 9/2014 |
| GB | 201413030 | 9/2014 |
| GB | 201413032 | 9/2014 |
| GB | 201413034 | 9/2014 |
| GB | 201413036 | 9/2014 |

(56) References Cited

FOREIGN PATENT DOCUMENTS

| | | |
|---|---|---|
| GB | 201413037 | 9/2014 |
| GB | 2513061 A | 10/2014 |
| GB | 2523585 A | 9/2015 |
| GB | 2523585 A8 | 9/2015 |
| GB | 2525080 A | 10/2015 |
| GB | 2525294 A | 10/2015 |
| GB | 2525295 A | 10/2015 |
| GB | 2525480 A | 10/2015 |
| GB | 2525722 A | 11/2015 |
| GB | 2525723 A | 11/2015 |
| GB | 2525724 A | 11/2015 |
| GB | 2525725 A | 11/2015 |
| GB | 2525726 A | 11/2015 |
| GB | 2525727 A | 11/2015 |
| GB | 2529919 A | 3/2016 |
| GB | 2531633 A | 4/2016 |
| HK | 1197203 A1 | 1/2015 |
| HK | 1198138 A1 | 3/2015 |
| HK | 1198142 A1 | 3/2015 |
| HK | 1198143 A1 | 3/2015 |
| HK | 1200128 A1 | 7/2015 |
| HK | 1200129 A1 | 7/2015 |
| HK | 1203128 A1 | 10/2015 |
| IL | 233651 | 8/2014 |
| IL | 233896 | 9/2014 |
| IL | 230930 A | 6/2017 |
| IL | 233851 A | 6/2019 |
| IL | 233653 A | 4/2020 |
| IL | 233885 A | 5/2020 |
| IL | 233894 A | 5/2020 |
| IL | 233895 A | 5/2020 |
| JP | S5736898 U | 2/1982 |
| JP | S6033891 U | 3/1985 |
| JP | H022331 A | 1/1990 |
| JP | 2006503572 A | 2/2006 |
| JP | 2010506594 A | 3/2010 |
| JP | 2014524313 A | 9/2014 |
| JP | 2014532433 A | 12/2014 |
| JP | 2015503335 A | 2/2015 |
| JP | 2015505474 A | 2/2015 |
| JP | 2015505475 A | 2/2015 |
| JP | 2015505476 A | 2/2015 |
| JP | 2015506182 A | 3/2015 |
| JP | 2015508641 A | 3/2015 |
| JP | 2015512617 A | 4/2015 |
| JP | 2015513393 A | 5/2015 |
| JP | 2016509852 A | 4/2016 |
| JP | 2016517701 A | 6/2016 |
| KR | 20140070543 A | 6/2014 |
| KR | 20140090138 A | 7/2014 |
| KR | 20140125822 A | 10/2014 |
| KR | 20140125827 A | 10/2014 |
| KR | 20140125828 A | 10/2014 |
| KR | 20140125829 A | 10/2014 |
| KR | 20140127288 A | 11/2014 |
| KR | 20150003845 A | 1/2015 |
| KR | 20150005514 A | 1/2015 |
| KR | 20150035488 A | 4/2015 |
| MA | 20150054 A1 | 2/2015 |
| MA | 20150055 A1 | 2/2015 |
| MA | 20150056 A1 | 2/2015 |
| MA | 20150057 A1 | 2/2015 |
| MA | 20150058 A1 | 2/2015 |
| MA | 20150153 A1 | 5/2015 |
| MA | 20150169 A1 | 6/2015 |
| MX | 2014009396 A | 2/2015 |
| MX | 2014009398 A | 2/2015 |
| MX | 2014009393 A | 5/2015 |
| MX | 2014009394 A | 5/2015 |
| MX | 2014009397 A | 5/2015 |
| NZ | 627439 A | 9/2015 |
| NZ | 628058 A | 1/2016 |
| RU | 157882 U1 | 12/2015 |
| RU | 2581999 C2 | 4/2016 |
| SG | 2014013627 A | 7/2014 |
| TW | 201315397 A | 4/2013 |
| WO | WO-2010045671 A1 | 4/2010 |
| WO | WO-2012156695 A1 | 11/2012 |
| WO | WO-2013020280 A1 | 2/2013 |
| WO | WO-2013025921 A1 | 2/2013 |
| WO | WO-2013068081 A1 | 5/2013 |
| WO | WO-2013068100 A1 | 5/2013 |
| WO | WO-2013098405 A2 | 7/2013 |
| WO | WO-2013116558 A1 | 8/2013 |
| WO | WO-2013116561 A1 | 8/2013 |
| WO | WO-2013116565 A1 | 8/2013 |
| WO | WO-2013116567 A1 | 8/2013 |
| WO | WO-2013116568 A2 | 8/2013 |
| WO | WO-2013116571 A1 | 8/2013 |
| WO | WO-2013116572 A1 | 8/2013 |
| WO | WO-2013120566 A2 | 8/2013 |
| WO | WO-2013121608 A1 | 8/2013 |
| WO | WO-2013138384 A2 | 9/2013 |
| WO | WO-2013138384 A3 | 10/2013 |
| WO | WO 2013156339 | 10/2013 |
| WO | WO-2013179524 A1 | 12/2013 |
| WO | WO-2014116974 A1 | 7/2014 |
| WO | WO-2014140273 A2 | 9/2014 |
| WO | WO-2014158051 A1 | 10/2014 |
| WO | WO-2013116568 A3 | 11/2014 |
| WO | WO-2014184239 A1 | 11/2014 |
| WO | WO-2015013108 A2 | 1/2015 |
| WO | WO-2015013108 A3 | 4/2015 |
| WO | WO-2015047954 A1 | 4/2015 |
| WO | WO-2015128665 A1 | 9/2015 |
| WO | WO-2015128666 A1 | 9/2015 |
| WO | WO-2015128667 A1 | 9/2015 |
| WO | WO-2016024083 A1 | 2/2016 |
| WO | WO 2016076178 | 5/2016 |
| WO | WO-2016135342 A2 | 9/2016 |
| WO | WO-2017149152 A1 | 9/2017 |
| WO | WO-2017160559 A1 | 9/2017 |

OTHER PUBLICATIONS

International Search Report and Written Opinion, Application No. PCT/EP2017/072813, dated Dec. 11, 2017, 3 pages.
Application and File History for U.S. Appl. No. 16/333,570, filed Mar. 24, 2019, Inventor: Hepworth et al.
Application and File History for U.S. Appl. No. 16/333,567, filed Mar. 24, 2019, Inventor: Hepworth et al.
Communication pursuant to Article 94(3) EPC for Application No. 1778008.3, dated Sep. 11, 2020, 8 pages.
International Preliminary Report on Patentability for Application No. PCT/EP2017/073057, dated Mar. 28, 2019, 9 pages.
International Preliminary Reporton Patentability for Application No. PCT/EP2017/072811, dated Aug. 20, 2018, 7 pages.
International Preliminary Report on Patentability for Application No. PCT/EP2017/072814, dated Nov. 30, 2018, 8 pages.
International Preliminary Report on Patentabilityfor Application No. PCT/EP2017/073061, dated Mar. 28, 2019, 7 pages.
International Search Report and Written Opinion for Application No. PCT/EP2017/072811, dated Dec. 11, 2017, 15 pages.
International Search Report and Written Opinion for Application No. PCT/EP2017/072814, dated Dec. 11, 2017, 12 pages.
International Search Report and Written Opinion for Application No. PCT/EP2017/073057, dated Feb. 7, 2018, 16 pages.
International Search Report and Written Opinion for Application No. PCT/EP2017/073061, dated Jan. 8, 2018, 13 pages.
Office Action For Korean Application No. 10-2019-7010649, dated Jan. 19, 2021, 7 pages.
Office Action dated Jul. 21, 2020 for European Application No. 17780009.1, 7 pages.
Search Report dated Mar. 2, 2018 for Great Britain Application No. GB1615609.3, 4 pages.

* cited by examiner

RECEPTACLE SECTION

PRIORITY CLAIM

The present application is a National Phase entry of PCT Application No. PCT/EP2017/072813, filed Sep. 12, 2017, which claims priority from GB Patent Application No. 1615620.8, filed Sep. 14, 2016, which is hereby fully incorporated herein by reference.

TECHNICAL FIELD

The present disclosure relates to a receptacle section, and more particularly to a receptacle section for an aerosol provision article.

BACKGROUND

Smoking articles such as cigarettes, cigars and the like burn tobacco during use to create tobacco smoke. Attempts have been made to provide alternatives to these articles that burn tobacco by creating products that release compounds without burning.

Examples of such products are heating devices which release compounds by heating, but not burning, the material. The material may be for example tobacco or other non-tobacco products, which may or may not contain nicotine.

As another example, there are aerosol provision articles such as so-called e-cigarette devices. These devices typically contain a liquid which is heated to vaporize the liquid to produce an inhalable vapor or aerosol. The liquid may contain nicotine and/or flavorings and/or aerosol-generating substances, such as glycerol. The known e-cigarette devices typically do not contain flavorings other than those in the liquid.

SUMMARY

According to a first aspect of the present disclosure, there is provided a receptacle section for an aerosol provision article, the aerosol provision article for generating a flow of aerosol in use, the receptacle section arranged for having installed therein an activatable element for modifying, once activated, a property of said flow of aerosol, the receptacle section being arranged to apply, on installation of said activatable element in the receptacle section by a user, a force to said activatable element to activate said activatable element.

The receptacle section may comprise a first portion and a second portion, the second portion being moveable relative to the first portion between a first position and a different, second position, and movement of the second portion from the first position to the second position may cause said force to be applied to activate said activatable element when said activatable element is installed in the receptacle section.

The first position may be for allowing insertion of said activatable element in the receptacle section by a user.

When the second portion is in the second position the receptacle section may define a flow path for said aerosol to flow through the receptacle section via said activatable element installed in the receptacle section in use.

The receptacle section may comprise at least one activating element operable to move between a first element position and a different, second element position, and movement of the second portion from the first position to the second position may cause the at least one activating element to move from the first element position to the second element position, and movement of the activating element from the first element position to the second element position may cause said force to be applied to said activatable element installable in the receptacle section.

The receptacle section may define a channel for receiving said activatable element, and the at least one activating element may comprise a resilient member extending along at least a portion of the channel, and the resilient member may be operable to bend between the first element position and the second element position, and in the second element position at least a portion of the resilient member may protrude into the channel, thereby to apply said force to activate said activatable element received in the channel in use.

The resilient member may comprise an inward protruding portion protruding from the resilient member towards the channel, the inward protruding portion being for contacting said activatable element received in the channel in use, thereby to apply said force to activate said activatable flavor element received in the channel in use.

One of the first portion and the second portion may comprise the at least one resilient member, and the at least one resilient member may be receivable in the other of the first portion and the second portion, and the resilient member may comprise an outward protruding portion, the outward protruding portion protruding out from the resilient member away from the channel and for contacting an inner wall of the other of the first portion and the second portion, and said movement of the second portion from the first position to the second position may cause the outward protruding portion to contact the other of the first portion and the second portion, thereby to bend the resilient member from the first element position to the second element position.

The inner wall of the other of the first portion and the second portion may comprise an inward protruding portion protruding out of the inner wall towards the resilient member, for contacting the outward protruding portion of the resilient member.

The second portion may be slidably mounted to the first portion thereby to allow sliding of the second portion relative to the first portion, parallel to the longitudinal axis of the receptacle section, between the first position and the second position.

The second portion may be receivable in the first portion, and a side wall of the second portion may define an opening, and when the second portion is in the first position, the opening may be exposed for insertion and/or removal of said activatable element into the channel through the opening, and when the second portion is in the second position, the opening may be closed off by the first portion.

The second portion may be removable from the first portion.

The second portion may be rotatable with respect to the first portion about a longitudinal axis of the receptacle section, and the second portion may define a first inner radial dimension and a second, smaller inner radial dimension, and the second portion may be operable by a user to rotate between the first position and the second position, and in the first position the first inner radial dimension may be rotationally aligned with the resilient member, and in the second position the second inner radial dimension may be rotationally aligned with the resilient member, and rotation of the second portion from the first position to the second position may cause the resilient member to bend from the first element position to the second element position, thereby to apply said force to activate said activatable element received in the channel in use.

The inner radial dimension of the second portion may vary gradually from the first inner radial dimension to the second inner radial dimension.

The second portion may be received in the first portion, and when the second portion is in the first portion, an opening in a side wall of the first portion may be aligned with an opening in a side wall of the second portion to allow insertion and/or removal of said activatable element into and/or from the channel, through the opening of the first portion and the opening of the second portion, and when the second portion is in the second position, the opening of the first portion and the opening of the second portion may be misaligned such that the side wall of the second portion closes off the opening of the first portion.

The receptacle section may comprise at least two said resilient members, and a first said resilient member may be located on an opposite side of the channel to a second said resilient member.

The second portion may be slidable in the first portion, between the first position and the second position, substantially parallel to a longitudinal axis of the receptacle section, and the receptacle section may comprise a third portion for closing off an opening in a side wall of the second portion, the third portion comprising an inward protruding portion for contacting and applying said force to activate said breakable flavor element received in the second portion, the third portion being pivotally mounted to the second portion about an axis substantially perpendicular to the longitudinal axis of the receptacle section, thereby allowing pivoting of the third portion between an open position for allowing insertion of said activatable element into the second portion via the opening, and a closed position for closing off the opening and for applying said force, via the inward protruding portion, to activate said activatable element received in the second portion in use.

Movement of the second portion from the first position to the second position may cause the third portion to pivot from the open position to the closed position.

The second portion may be pivotally mounted to the first portion, thereby to allow pivoting of the second portion relative to the first portion, about an axis substantially perpendicular to the longitudinal axis of the receptacle section, between the first position and the second position.

The second portion may comprise an inward protruding portion for applying said force to said activatable element, and a side wall of the first portion may define an opening allowing, when the second portion is in the first position, insertion and/or removal of said activatable element into and/or from the receptacle section, through the opening, and when the second portion is pivoted to the second position the second portion may close off the opening and the inward protruding portion may apply said force to activate said activatable element.

The activatable element may be installed in the receptacle section.

The activatable element may comprise a substance for modifying said property of the aerosol, and said force may cause the substance to be exposed, thereby to modify said property of said flow of aerosol.

The activatable element may comprise a breakable capsule in which the substance is contained, and said force may break the capsule thereby to expose the substance.

The breakable capsule may be held in a carrier material, and the substance may be a liquid and/or gel, and said force may break the breakable capsule to release the liquid and/or gel into the carrier material.

The property may be one or more of an organoleptic property of the aerosol, a flavor of the aerosol, and the pH of the aerosol.

According to a second aspect of the present disclosure, there is provided a mouthpiece for an aerosol provision article, said aerosol provision article being for generating a flow of aerosol in use, the mouthpiece comprising the receptacle section according to the first aspect.

According to a third aspect of the present disclosure, there is provided an aerosol provision article for generating a flow of aerosol in use, the aerosol provision article comprising the receptacle section according to the first aspect, and/or the mouthpiece according to the second aspect.

The aerosol provision article may comprise: a container for holding a liquid or a material; a heater for volatilizing liquid held in the container to generate said flow of aerosol in use or for heating but not combusting the material to generate said flow of aerosol in use.

Further features and advantages of the disclosure will become apparent from the following description of embodiments of the invention, given by way of example only, which is made with reference to the accompanying drawings.

BRIEF DESCRIPTION OF THE DRAWINGS

FIG. 1 shows a schematic cross section of an aerosol provision article according to an example.

FIG. 2*a* shows a schematic perspective view of a part of an aerosol provision article comprising a first receptacle section according to a first example.

FIGS. 2*b*, 2*c*, and 2*e* show schematic cross sections of the first receptacle section according to the first example in different configurations.

FIGS. 2*d* and 2*f* show schematic cross sections of the first receptacle section according to the first example shown in FIGS. 2*c* and 2*e* respectively, but in a plane perpendicular to the plane of the cross sections shown in FIGS. 2*c* and 2*e*, respectively.

FIGS. 3*a* to 3*c* show schematic cross sections of a part of an aerosol provision article comprising a second receptacle section according to a second example, in different configurations.

FIGS. 4*a* and 4*b* show schematic perspective views of a part of an aerosol provision article comprising a third receptacle section according to a third example, in different configurations.

FIGS. 4*c* and 4*e* show schematic cross sections of the third receptacle section according to the third example shown in FIGS. 4*a* and 4*b*, respectively.

FIGS. 4*d* and 4*f* show schematic cross sections of the third receptacle section according to the third example shown in FIGS. 4*c* and 4*e* respectively, but in a plane perpendicular to the plane of the cross sections shown in FIGS. 4*c* and 4*e*, respectively.

FIGS. 5*a* and 5*b* show schematic cross sections of a part of an aerosol provision article comprising a fourth receptacle section according to a fourth example, in different configurations.

FIGS. 6*a* and 6*b* show schematic cross sections of a part of an aerosol provision article comprising a fifth receptacle section according to a fifth example, in different configurations.

DETAILED DESCRIPTION

Referring to FIG. 1, a schematic of an example aerosol provision article 100 is illustrated. The aerosol provision article 100 is an inhalation device (i.e. a user uses it to inhale an aerosol provided by the device). The aerosol provision article is hand-held. In this example, the article 100 is an electronic cigarette device 100. In broad outline, the device 100 volatilizes a liquid to form a vapor or an aerosol which passes through an activatable element 124 received in a receptacle section 102 of the device 100. In this example the receptacle section 102 is a mouthpiece of the device 102. The activatable element 124, once activated, modifies a property of the vapor or aerosol passing through the mouthpiece 102 for inhalation by a user. For example, the activatable element 124 may be a breakable flavor element 124 which, once broken, imparts a flavor to the vapor or aerosol passing through the mouthpiece 102 for inhalation by a user.

In this respect, first it may be noted that, in general, a vapor is a substance in the gas phase at a temperature lower than its critical temperature, which means that for example the vapor can be condensed to a liquid by increasing its pressure without reducing the temperature. On the other hand, in general, an aerosol is a colloid of fine solid particles or liquid droplets, in air or another gas. A colloid is a substance in which microscopically dispersed insoluble particles are suspended throughout another substance.

Returning to FIG. 1, the device 100 comprises an outer body 106 housing a liquid container 122 containing liquid 116, an atomizer 108, and a battery portion 112. The atomizer 108 is (electrically) connected to the battery portion 112.

The mouthpiece 102, in this example, is removably connected to the outer body 106. The mouthpiece 102 may be removed from the outer body 106, for example to allow access to the liquid container 122, for example to refill the liquid 116 held in the liquid container 122. The mouthpiece 102 has a channel 132 running there through that defines a flow path for a flow of vapor or aerosol. The mouthpiece 102 has removably received in the channel 132 a breakable flavor element 124 for imparting, once broken, a flavor to said flow of aerosol or vapor that passes through the mouthpiece 102 in use.

The breakable flavor element 124 may comprise flavored materials that, once the breakable flavor element is broken (e.g. crushed, pierced, mechanically activated), may be used to create a desired taste or aroma, or other properties, such as nicotine content. In this example, the breakable flavor element 124 comprises a breakable flavor capsule 126 for releasing, when broken for example by a user, a flavorant such as a liquid and/or a gel for imparting a flavor to a flow of at least one of a vapor and an aerosol. In this example, the breakable flavor element 124 comprises a breakable flavor capsule 126 wrapped or embedded in a carrier material. The carrier material may be any suitable material, for example, cellulose acetate. When the breakable flavor element 124, and hence the flavor capsule 126, is broken (e.g. crushed, pierced, mechanically activated), the flavorant such as a liquid and/or gel contained in the flavor capsule 126 is released into the carrier material so as to flavor vapor or aerosol passing there through.

The breakable flavor element 124 may be porous, for example so as allow vapor or aerosol to pass through it. The breakable flavor element 124 may be self-supporting, so as to be easily handled by a user (for example easily inserted and/or removed from the mouthpiece 102). For example the breakable flavor element 124 may comprise material wrapped partially or wholly in a wrapper, and/or the breakable flavor element 124 may be supported in a resilient housing, for example a plastic housing (not shown). As mentioned above, the breakable flavor element 124 may comprise, for example, a carrier material, such as cellulose acetate or the like. This carrier material may itself be flavored. The breakable flavor element 124 may be cylindrical, and/or comprise a cylindrical portion, so as to fit easily and/or tightly into a corresponding cylindrical channel 132 of the mouthpiece 102.

The device 100 is arranged so that, in use, as the liquid 116 is volatilized so as to produce an aerosol of liquid droplets or sufficiently heated to produce a vapor, at least some, all or substantially all of the aerosol or vapor passes through the breakable flavor element 124 received in the mouthpiece 102 for example so as to entrain constituents of the flavor element 134 therein. In some examples, a vapor is produced that then at least partly condenses to form on aerosol before exiting the device 100.

The liquid container 122 is provided generally centrally of the outer body 106. The liquid container 122 is annular in shape and defines a channel 104 running through the length of the liquid container 122. The liquid container 122 may be formed of rigid, watertight and airtight materials, such as metal, suitable plastics, etc. It will be appreciated that the liquid container 122 may have a different shape, such as conical, frustroconical, or combination of these, etc.

The atomizer 108 is provided with a heater 110 and a wick (not shown) in (thermal) contact with the heater 110. The orientation of the heater 110 is shown schematically and for example the heater 110 may be a coil having its longitudinal axis perpendicular or parallel to the longitudinal axis of the liquid container 108. The wick (not shown) is in contact with the liquid 116. This may be achieved by for example by the wick (not shown) being inserted through a through hole (not shown) in an end wall 122b of the liquid container 122. Alternatively or additionally, the end wall 122b may be a porous member which allows liquid to pass through from the liquid container 122, and the wick (not shown) may be in contact with the porous end wall 122b. The end wall 122b may be for example in the form of a porous ceramic disk. A porous end wall 122b of this type helps to regulate the flow of liquid onto the wick (not shown). The wick (not shown) is generally absorbent and acts to draw in liquid 116 from the liquid container 122 by capillary action (shown in FIG. 1 by arrows A). The wick can be non-woven and may be for example a cotton or wool material or the like, or a synthetic material, including for example polyester, nylon, viscose, polypropylene or the like, or a ceramic material.

The atomizer 108 is (electrically) connected to a battery in the battery portion 116 to enable the heater 110 to be powered. When the heater 110 is powered (which may be instigated for example by the user operating a button (not shown) of the device 100 or by a puff detector (not shown) of the overall device 100, as is known per se, liquid 116 is drawn (shown in FIG. 1 by arrows A) in from the liquid container 122 by the wick and is heated by the heater 110 to volatilize or vaporize the liquid, so as to generate at least one of a vapor and an aerosol.

As the user draws on the mouthpiece 102, air is drawn through an air inlet 118. The liquid 116 is volatized or vaporized by the heater 110 into air from the air inlet 118 thereby to produce a flow of one of a vapor and an aerosol. The flow of vapor or aerosol is drawn through the channel 104 of vapor liquid container 122, into the channel 132 of the mouthpiece 102, through the flavor element 134 received in the mouthpiece 102, and out from the device 100 for inhalation by a user (shown by arrow B in FIG. 1). The vapor or aerosol picks up (entrains) flavor (and/or other constituents) from the breakable flavor element 124 (for example once the breakable flavor element 124 is broken). One or more constituents of the breakable flavor element 124 is thereby mixed with the flow of at least one of a vapor and an aerosol. In examples where the breakable flavor element 124 contains or includes nicotine, the vapor or aerosol may thereby also contain nicotine entrained from the breakable flavor element 124. A one way valve (not shown) may be provided, for example at or near an upper end 122a of the liquid container 122, so that the vapor or aerosol can only exit the channel 104 and cannot back-flow to the heater 110 or the electronics (not shown) of the device 100.

The breakable flavor element 124 may be or comprise material that may be used to impart a flavor (and/or one or more other constituents) to the aerosol or vapor. In some examples, the one or more constituents of the breakable flavor element 124 may comprise constituents inherent to the material itself. The material may for example consist of or comprise tobacco. As the aerosol or vapor passes through and over the tobacco, the aerosol or vapor entrains organic and other compounds or constituents from the tobacco that lend tobacco its organoleptic properties, thus imparting the flavor to the aerosol or vapor. It will be understood however that materials other than tobacco may be used to impart different flavors (and/or one or more other constituents) to the aerosol or vapor flow. The flavor element 124 may comprise constituents added to a material of the flavor element 124.

Nicotine may be provided in the liquid 116. Accordingly, where it is intended that the device 100 provides nicotine for the user, the nicotine may be provided in the liquid 116, may be obtained from the flavor element 124, or any combination of these. Likewise, flavorings may be added to the flavor element 124 (whether or not the flavor element 124 is or includes tobacco) and/or to the liquid 116. A material of the flavor element 124 may be a solid material, or be a mixture of solid materials, one or more of each comprising one or more constituents that can be mixed with the flow of vapor or aerosol. It will be appreciated that the flavor element 124 may comprise one or more other constituents that are not entrained into the aerosol or vapor passing there through. It will also be appreciated that the flavor element 124 may comprise a portion that does not impart any flavor and/or release any constituents into the flow of a vapor or an aerosol.

Various receptacle sections for use with an aerosol provision article (e.g. device 100 in FIG. 1) will now be described. In broad overview, the various receptacle sections are arranged for having installed therein a breakable flavor element for releasing, once crushed, a flavorant for imparting a flavor to a flow of at least one of a vapor and an aerosol. The various receptacle sections are each arranged to break, on installation of said breakable flavor element in the receptacle section by a user, the breakable flavor element. The various receptacle sections provide a convenient way for a user to break a breakable flavor element during (e.g. on, or simultaneously with) the act of installing the breakable flavor element in an overall aerosol provision article (e.g. device 100 in FIG. 1). The breakable flavor element being broken (e.g. crushed, pierced, or otherwise mechanically activated) by the receptacle section on (during) installation of the breakable flavor element into the receptacle section reduces time and effort associated with, for example, a separate crushing operation, for example a user breaking the breakable flavor element manually before installation into an aerosol provision article (e.g. device 100 in FIG. 1).

For reasons of convenience, as used herein the term aerosol should be taken as encompassing an aerosol, a vapor or a mixture of an aerosol and vapor.

Turning first to FIGS. 2a to 2f there is illustrated schematically a perspective view and cross sections of part of a device 200 that comprises an example receptacle section 202. In this example, the receptacle section 202 is a mouth-end section 202 of the device 200, that is, the receptacle section 202 is located toward an end of the device 200 for receipt into a user's mouth in use. In some examples, the mouth-end section 202, or at least a portion thereof, is a mouthpiece 202. In other examples, the receptacle section 202 may be at a different location in the overall device 200, for example intermediate of the body and the mouthpiece. For brevity, features in FIG. 2 and the functioning thereof that are the same or similar to those features already described with reference to FIG. 1 are given similar reference numerals to as in FIG. 1 but increased by 100, and will not be described in detail again.

The mouth-end section 202 has the general form of an elongate hollow cylinder. The mouth-end section 202 comprises a first portion 202a and a second portion 202b moveable relative to the first portion 202a. The second portion 202b is moveable relative to the first portion 202a between a first position (see FIGS. 2a and 2b) and a different, second position (see FIGS. 2e and 2f). The first position (see FIGS. 2a and 2b) is for allowing insertion of a breakable flavor element 224 in the receptacle section 202 by a user. When the second portion 202b is in the second position (see FIGS. 2e and 2f) the receptacle section 202 defines a flow path or closed channel for an aerosol to flow through the receptacle section 202 via a breakable flavor element installed in the receptacle section 202 in use. Movement of the second portion 202b from the first position to the second position simultaneously breaks and installs a breakable flavor element into the receptacle section 202.

Figure 2A:
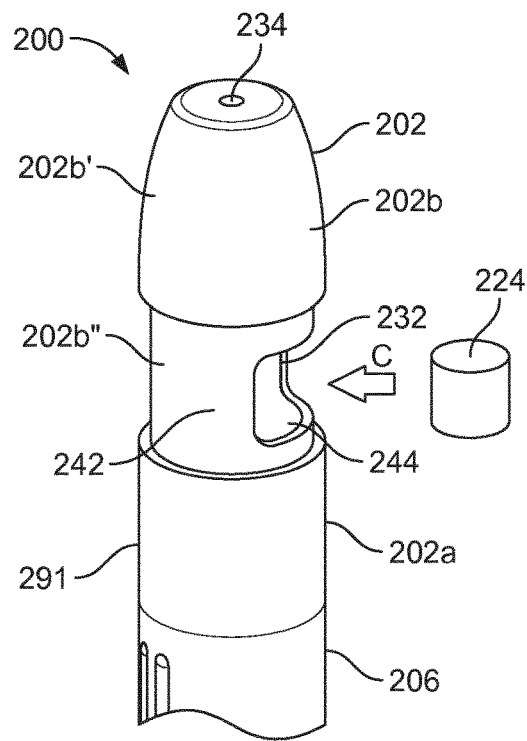
Figure 2B:
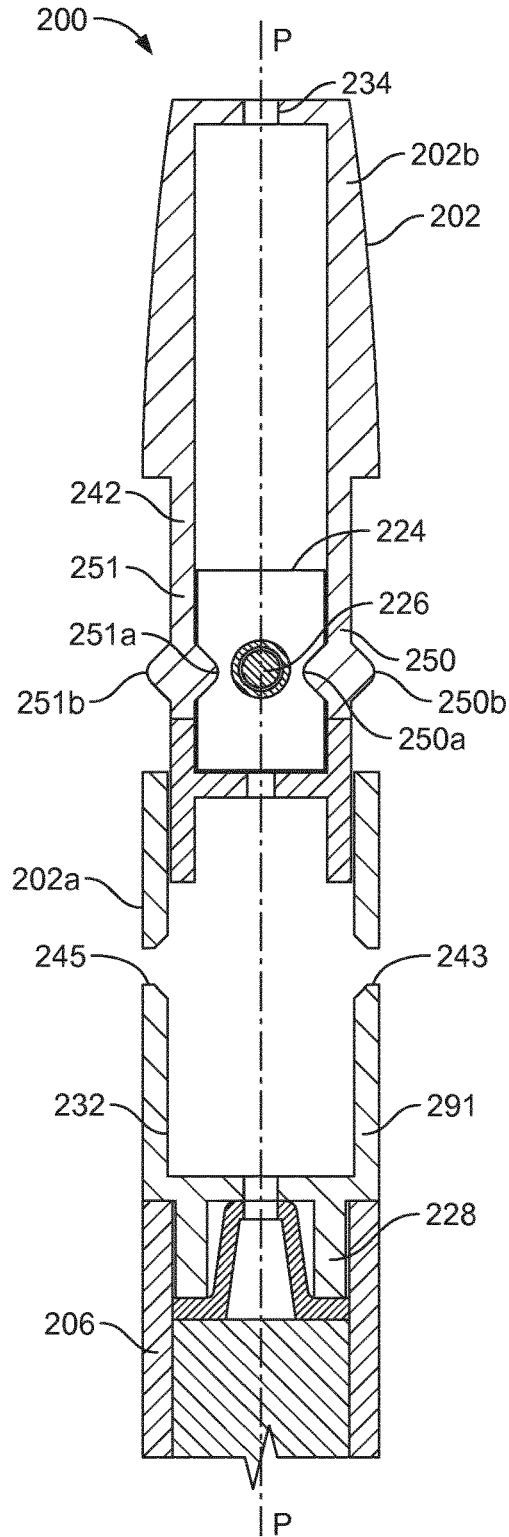
Figure 2C:
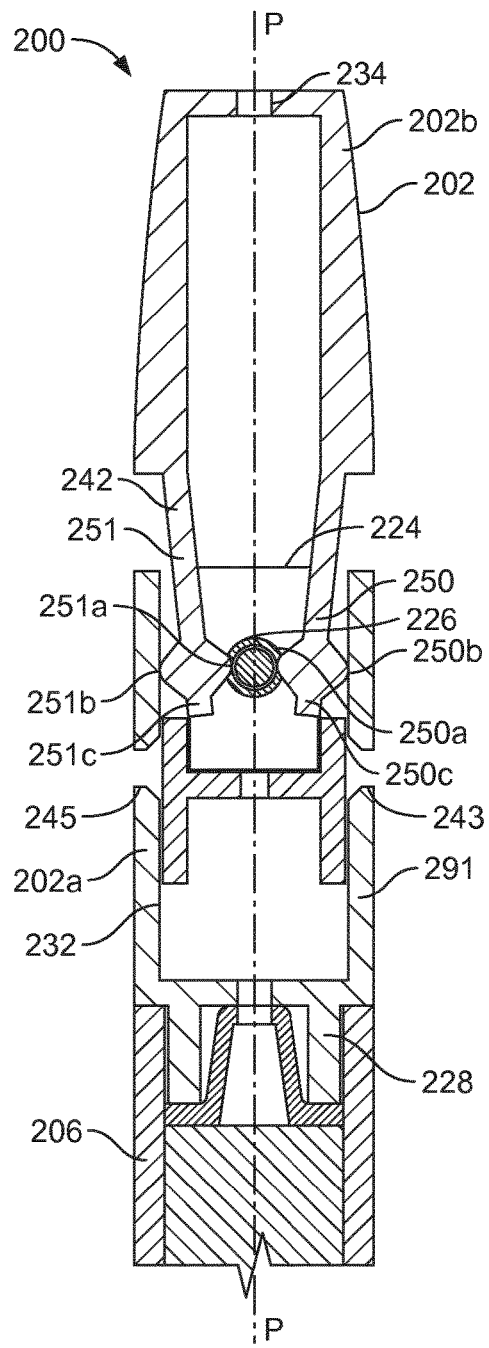
Figure 2D:
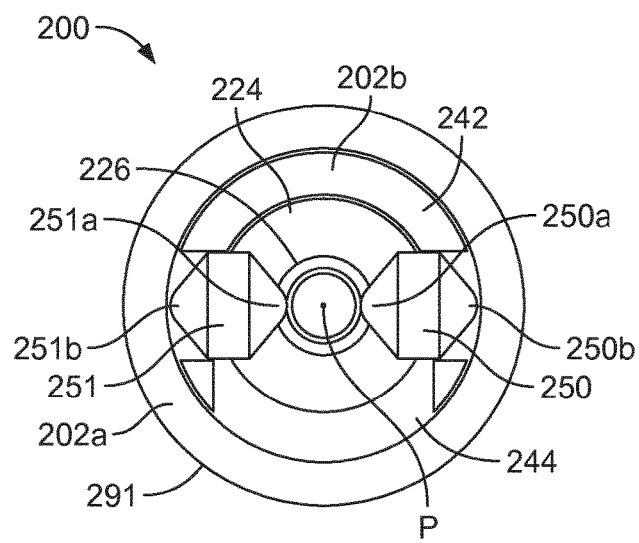
Figure 2E:
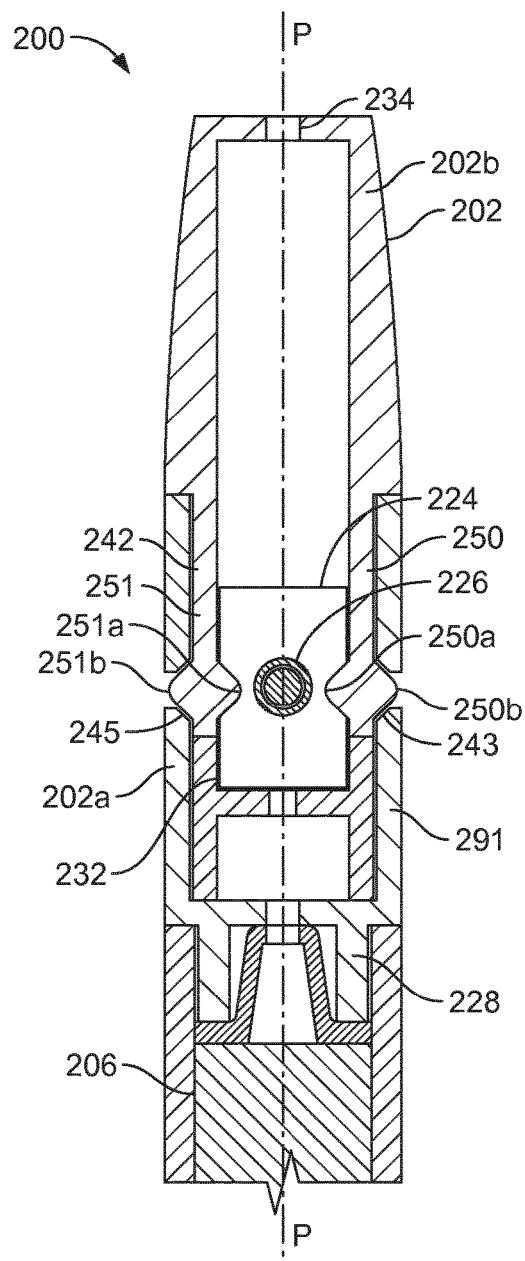
Figure 2F:
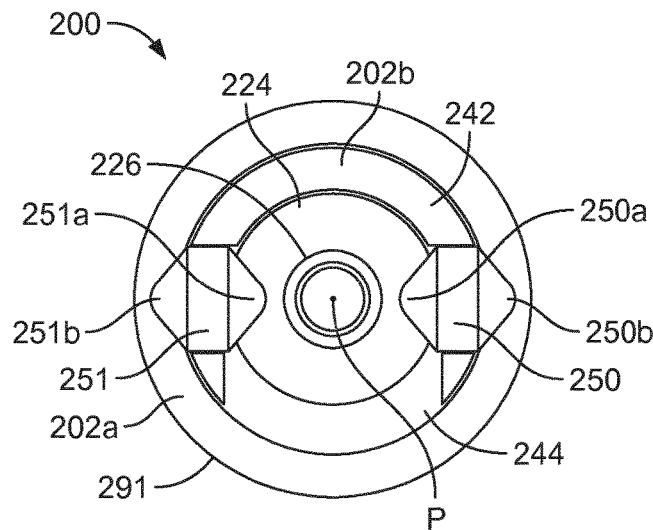

The second portion 202b is slidably mounted to the first portion 202a thereby to allow sliding of the second portion relative to the first portion, substantially parallel to the longitudinal axis P-P of the mouth-end section 202, between the first position (see FIGS. 2a and 2b) and the second position (see FIGS. 2e and 2f).

The mouth-end section 202 is arranged to allow, when the second portion 202b is in the first position (see FIGS. 2a and 2b), insertion and/or removal of a breakable flavor element 224 into and/or from the mouth-end section 202 in a direction substantially perpendicular to the longitudinal axis P-P of the mouth-end section 202.

The first portion 202a and the second portion 202b are generally elongate and are hollow. The first portion 202a extends from the body portion 206 of the device 200 and connects, for example by a screw thread 228, to the body portion 206. The second portion 202b comprises a first part 202b' and a second part 202b" that extends from the first part 202b' and has a slightly narrower diameter than does the first part 202b' and which is slidably received in the first portion 202a. The mouth-end section 202 defines a flow channel 232 internally thereof. The first part 202b' of the second portion 202b is for receipt into a user's mouth. The first part 202b' of the second portion 202b has an outlet 234 allowing a user to inhale aerosol from the overall device 200 via the channel 232. A side wall 242 of the second part 202b" of the second portion 202b defines an opening 244 for insertion and/or removal of the flavor element 224, through the opening 244, into the channel 232 internal of the second portion 202b.

When the second portion 202b is in the first position (see FIGS. 2a and 2b) the first part 202b' of the second portion 202b is relatively distal from the first portion 202a, and the second part 202b" of the second portion 202b is exposed so that the opening 244 is exposed for insertion and/or removal of the flavor element 224 there through.

When the second portion 202b is in the second position (see FIGS. 2e and 2f), the first part 202b' of the second portion 202b abuts against the first portion 202a, and the second part 202b" of the second portion 202b is within the first portion 202a such that the opening 244 in the side wall 242 is closed off by the first portion 202a. The breakable element 224 is thereby installed into the mouth-end section 202.

The second portion 202b comprises breaking elements 250, 251 each operable to move between a first element position (see FIGS. 2a, 2b) and a different, second element position (see FIGS. 2c and 2d). Movement of the second portion 202b from the first position to the second position causes each breaking element 250, 251 to move from the first element position to the second element position. Movement of each breaking element 250, 251 from the first element position (see FIGS. 2a, 2b) to the second element position (see FIGS. 2c and 2d) breaks the breakable flavor element 234 received in the channel 232. It will be readily appreciated that although this example has two breaking elements 250, 251, in other examples there could instead be only one such breaking element, or more than two breaking elements.

Each breaking element 250, 251 comprises a resilient member 250, 251 extending along a portion of the channel 232 of the mouth-end section 202, i.e. extending along the channel 232 in a direction substantially parallel to the longitudinal axis P-P of the mouth-end section 202.

Each resilient member 250, 251 forms part of the side wall 242 of the second portion 202b. A distal end 250c, 251c of each of the resilient members 250, 251 is free to move relative to the side wall 242. The respective distal ends 250c, 251c of the resilient members 250, 251 are therefore operable to bend or flex between the first element position (see FIGS. 2a and 2b) and the second element position (see FIGS. 2c and 2d). In the first element position (FIGS. 2a and 2b) each resilient member 250, 251 lies substantially parallel with the channel 232. In the second position (FIGS. 2c and 2d) a portion 250a, 251a of each resilient member 250, 251 protrudes into the channel 232, thereby to break (e.g. crush) the breakable flavor element 224 received in the channel 232.

Each resilient member 250, 251 is receivable in the first portion 202a. Each resilient member 250, 251 comprises an outward protruding portion 250b, 251b protruding out from the respective resilient member 250, 251 away from the channel 232. The outward protruding portions 250b, 251b are for contacting an inner surface of the side wall 291 of the first portion 202a. Movement (in this example, sliding) of the second portion 202b from the first position (FIGS. 2a and 2b) towards the second position (see e.g. FIGS. 2c and 2d), along the longitudinal axis P-P of the mouth-end portion 202, causes the outward protruding portion 250b, 251b to contact the inner surface of the side wall 291 of the first portion 202a. The side wall 291 of the first portion 202a thereby causes (forces) each resilient member 250, 251 to bend into the channel 232, from the first element position to the second element position. This breaks (crushes) the breakable flavor element 224 between the resilient members 250, 251.

The side wall 291 of the first portion 202a has two apertures 243, 245 into which the outward protruding portions 250b, 251b of the respective resilient members 250, 251 can extend into, respectively, after the breakable flavor element 224 has been broken. When the outward protruding portions 250b, 251b extend into the respective apertures 243, 245, there is no longer a force on the resilient members 250, 251 bending them into the channel 232, and hence the resilient members 250, 251 relax (bend back) into the first element position (see FIGS. 2e and 2f), and the mouth-end section 202 is in the second position.

Each resilient member 250, 251 comprises, at an end 250c, 251c of the respective resilient member 250, 251 that is free to move, an inward protruding portion 250a, 251a protruding from the respective resilient member 250, 251 towards the channel 232. The inward protruding portion 250a, 251a is for contacting the breakable flavor element 224 received in the channel 232, thereby to break said breakable flavor element 224 received in the channel 232 when the respective resilient member 250, 251 is bent to the second element position (See FIGS. 2c and 2d). The resilient members 250, 251 are located on opposite sides of the channel 232 to one another. The respective inward protruding portions 250a, 251a therefore point towards each other. When the resilient members 250, 251 are bent from the first element position (FIGS. 2a and 2b) to the second element position (FIGS. 2c and 2d), the breakable flavor element 224 is therefore squeezed (and hence broken) between the inward protruding portions 250a, 251a. The inward protruding portions 250a, 251a may increase the lateral squeezing force exerted on the breakable flavor element 224 for a given longitudinal sliding force applied by a user to slide the second portion 202b towards the first portion 202b, and hence allow for easier breaking of a flavor element 224 on installation into a mouth-end section 202 of an overall device 200.

Although not illustrated, the inner surface of the side wall 291 of the first portion 202a may comprise inward protruding portions protruding out of the side wall 291 towards the resilient members 250, 251 for contacting the respective outward protruding portions 250a, 251a of the resilient members 250, 251. This may increase the extent to which the resilient members are bent, and hence may allow for more effective breaking of a flavor element 224 on installation into a mouth-end section 202 of an overall device 200.

Referring to the sequence illustrated in FIGS. 2a to 2f, the second portion 202b of the mouth-end section 202 is initially in the first position. The user may therefore insert (arrow C) a breakable flavor element 224, through the exposed opening 244 in the side wall 242 of the second portion 202b into the channel 232 (see FIG. 2a). Once the flavor element 224 is inserted (see FIG. 2b), the user may push or otherwise manipulate the first part 202b' of the second portion 202b towards the first portion 202a, so that the second part 202b" of the second portion 402b slides substantially parallel to axis P-P of the mouth-end section 202 into the first portion 202a. In doing so, the resilient members 250, 251 are bent laterally into the channel 232 from the first element position to the second element position via contact with the side wall 291 of the first portion 202a, and hence break the breakable flavor element 224 received in the channel 232 (See FIGS. 2c and 2d). On further pushing or otherwise manipulating the first part 202b' of the second portion 202b towards the first portion 202a, the second part 202b" of the second portion 202b slides substantially parallel to axis P-P of the mouth-end section 202 into the first portion 202a until the first part 202b' of the second portion 202b abuts against the first portion 202a. The outward protruding portions 250b, 251b of the resilient members 250, 251 extend into the respective apertures 243, 245, and thereby the resilient members 250, 251 relax (bend back) into the first element position (see FIGS. 2e and 2f). The mouth-end section 202 is thereby in the second position, and the breakable flavor element 224 is installed in the mouth-end section 202.

In use, when a user draws on the mouth-end section 202, air is drawn in through an air inlet (120 in FIG. 1), and a heater (110 in FIG. 1) volatizes liquid (116 in FIG. 1) held in the liquid container (122 in FIG. 1) into the inlet air to generate a flow of vapor or aerosol. The flow passes through the channel (104 in FIG. 1) in the liquid container (122 in FIG. 1), into the channel 232 of the mouth-end section 202, through the (broken) breakable flavor element 224, and exits from the outlet 234 of the second portion 202a for inhalation by the user. The flow of vapor or an aerosol through the (broken) breakable flavor element 224 thereby entrains one or more of the constituents released by the crushed flavor element 224 in the flow. This use description is applicable also to the other examples described herein, and so will not be described in detail again.

Figure 3A:
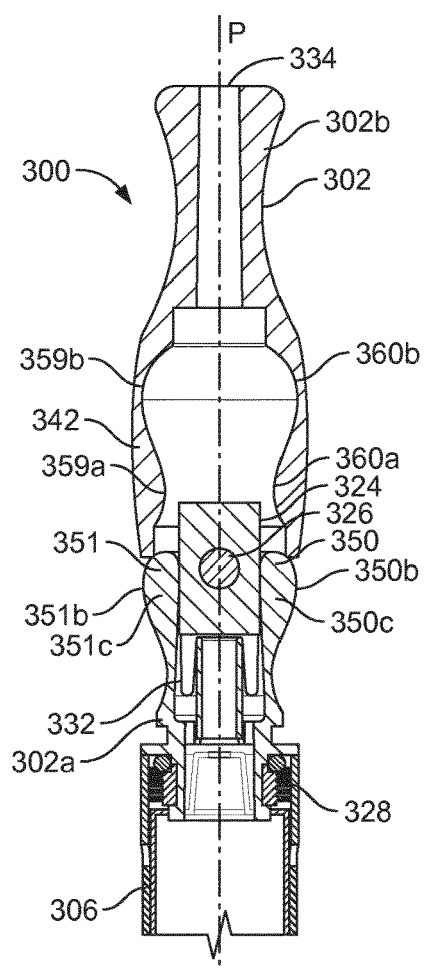
Figure 3B:
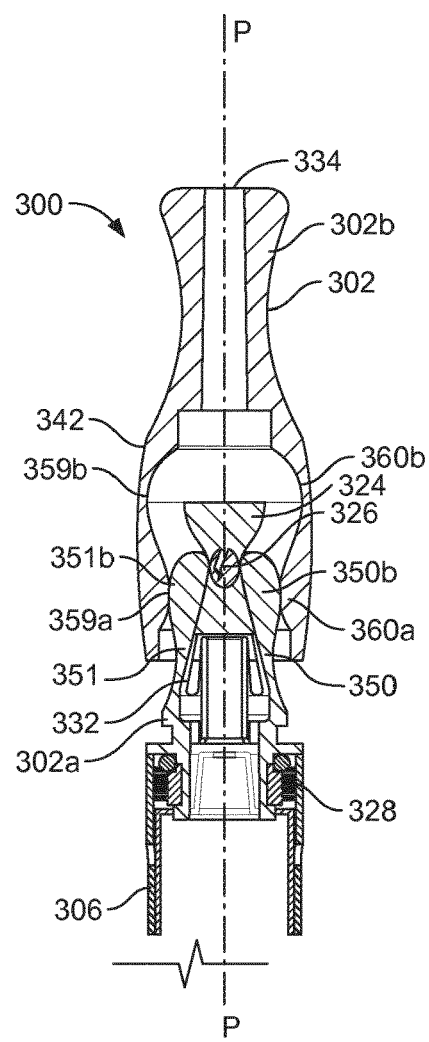
Figure 3C:
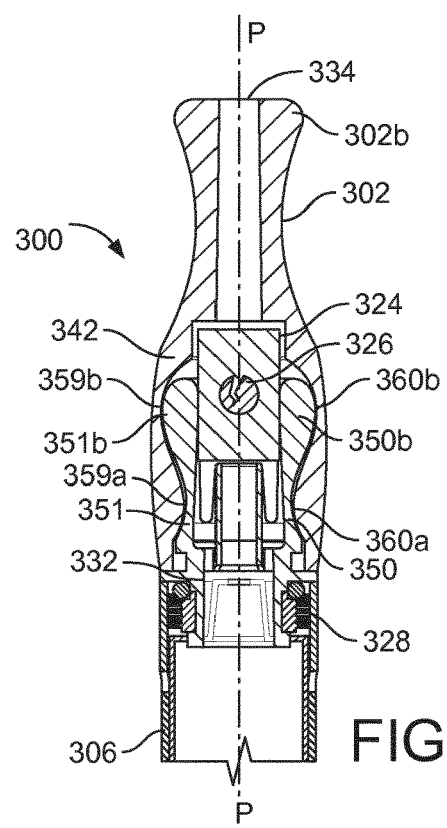

Referring now to FIGS. 3a to 3c, there is illustrated schematically cross sections of another example of a part of a device 300 comprising a receptacle section 302 in different configurations. The example receptacle section 302 in FIGS. 3a to 3c can be used, for example as illustrated in the FIGS. 3a to 3c as the mouth-end section 302 of the device 300, or as some other section of the overall device 300, for example, intermediate of the body 306 of the device 300 and the mouthpiece of the device 300. For brevity, features in FIG. 3 and the functioning thereof that are the same or similar to those features already described with reference to FIGS. 2a to 2f are given similar reference numerals to as in FIG. 2 but increased by 100, and will not be described in detail again.

As in the mouth-end section 202 illustrated in FIGS. 2a to 2f, the mouth-end section 302 illustrated in FIGS. 3a to 3c comprises a first portion 302a and a second portion 302b moveable relative to the first portion 302b substantially parallel to a longitudinal axis P-P of the mouth-end section 302, between an first position (see FIG. 3a) and a second position (see FIG. 3c). Again, the mouth end section 302 comprises resilient members 350, 351 extending along a portion of a channel 332 of the mouth-end section 302 into which a breakable flavor element 324 is received. The resilient members 350, 351 are bendable into the channel 332 from a first element position (see FIG. 3a) in which they are substantially parallel with a longitudinal axis P-P of the mouth-end section 302, and a second element position (see FIG. 3b) in which they are bent into the channel 332, thereby to break the breakable flavor element 324 received therein.

However, in this example, the resilient members 350, 351 extend from the first portion 302a. The first portion 302a is connectable via suitable connecting means 328 to the body 306 of the overall device 300. The resilient members 350, 351 are receivable in the second portion 302b. The second portion 302b is removable from the first portion 302a. When the second portion 302b is removed from the first portion 302a, the resilient members 350, 351 are exposed allowing a user to insert a breakable flavor element 324 between the resilient members 350, 351 into the channel 332.

As for the mouth-end section 202 illustrated in FIGS. 2a to 2f, the resilient members 350, 351 of the mouth-end section 302 illustrated in FIGS. 3a to 3c comprise respective outward protruding portions 350b, 351b at respective distal ends 350c, 351c that are free to move with respect to the first portion 302a.

The second portion 302b is elongate and hollow. The second portion 302b comprises an outlet 334 for allowing a user to inhale aerosol therefrom via the channel 332. The second portion 302b comprises inward protruding portions 359a, 360a protruding radially inwardly of the second portion 302b from a side wall 342 of the second portion 302b. The inward protruding portions 359a, 360a are for contacting the respective outward protruding portions 350a, 351a of the resilient members 350, 351. When the second portion 302b is moved axially towards the first portion 302a, the inward protruding portions 359a, 360a of the second portion 302b contact the respective outward protruding portions 350a, 351a of the resilient members 350, 351 of the first portion 302a, and hence bend the resilient members 350, 351 into the channel 332, hence breaking the breakable flavor element 324 received therein (see FIG. 3b).

The second portion 302b comprises recess portions 359b, 360b that define radial recesses in an inner surface of the side wall 324 of the second portion 302b. The recess portions 359b, 360b are relatively proximal as compared to the inward protruding portions 359a, 360a. That is, as the second portion 302b is slid over the first portion 302a in use, the resilient members 350, 351 experience the inward protruding portions 359a, 360a before the recess portions 359b, 360b. The recess portions 359b, 360b are for receiving the outward protruding portions 350a, 351a of the resilient members 350, 351 respectively. When the outward protruding portions 350a, 351a are received in the recess portions 359b, 360b, there is no longer a radial inward force bending the resilient members 350, 351 into the channel 332, and hence the resilient members 350, 351 relax (spring back) to the first element position (see FIG. 3c), i.e. relax to substantially parallel to the longitudinal axis P-P of the mouth-end section 302.

Referring to the sequence illustrated in FIGS. 3a to 3c, a user inserts a breakable flavor element 324 (comprising a breakable flavor capsule 326) into the channel 332 of the first portion, between the resilient members 350, 351. A user then aligns the second portion 302b with the first portion 302a in preparation for the resilient members 350, 351 of the first portion 302a to be received in the second portion 302 (see FIG. 3a). A user may then push or otherwise manipulate the second portion 302b towards (over) the first portion 302a substantially parallel to the longitudinal axis P-P of the mouth end section 302. In doing so, the inward protruding portions 359a, 360 of the second portion contact the outward protruding portions 350a, 351a of the resilient members 350, 351 and thereby bend the resilient members 350, 351 laterally into the channel 332, from the first element position to the second element position. The breakable flavor element 324 is thereby broken (crushed) between the resilient members 350, 351 (see FIG. 3b). On further pushing or otherwise manipulating the second portion 302b towards the first portion 302a, the second portion 302b slides substantially parallel to axis P-P of the mouth-end section 302 over the first portion 302a until the second portion 302b abuts against the first portion 302a. The outward protruding portions 350b, 351b of the resilient members 350, 351 are received into the respective recess portions 359b, 360b, and the resilient members 350, 351 thereby relax (bend back) into the first element position (see FIG. 3c). The second portion 302b is thereby in the second position, and the breakable flavor element 324 is both broken and installed in the mouth-end section 302. The mouth end section 302 is now ready to use.

Referring now to FIGS. 4a to 4f, there is illustrated schematically perspective views and cross sections of another example of a part of a device 400 comprising a receptacle section 402 in different configurations. The example receptacle section 402 in FIGS. 4a to 4f can be used, for example as illustrated in the FIGS. 4a to 4c as the mouth-end section 402 of the device 400, or as some other section of the overall device 400, for example, intermediate of the body 406 of the device 400 and the mouthpiece of the device 400. For brevity, features in FIG. 4 and the functioning thereof that are the same or similar to those features already described with reference to FIGS. 3a to 3c are given similar reference numerals to as in FIGS. 3a to 3c but increased by 100, and will not be described in detail again.

Figure 4A:
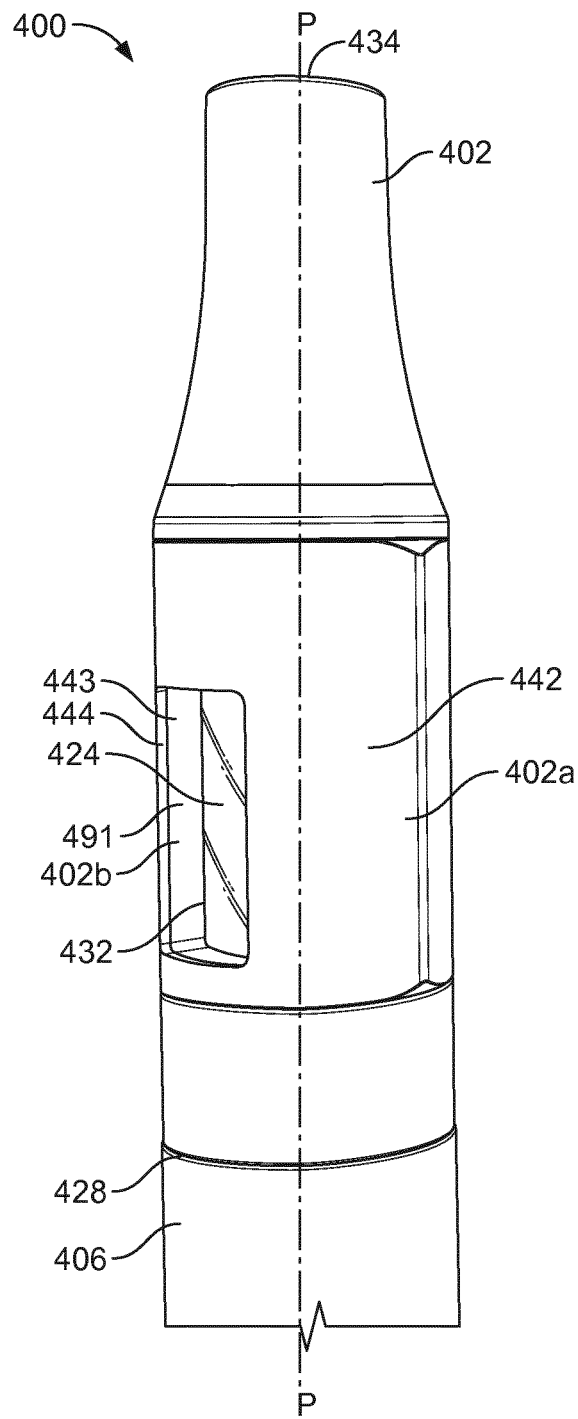
Figure 4B:
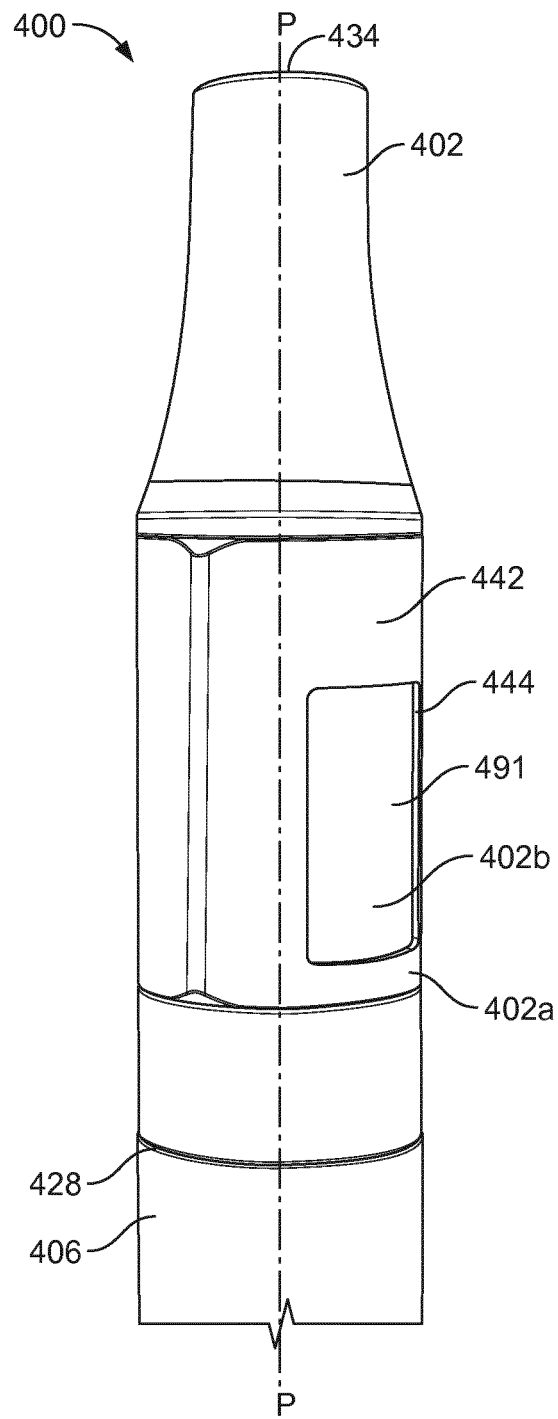
Figure 4C:
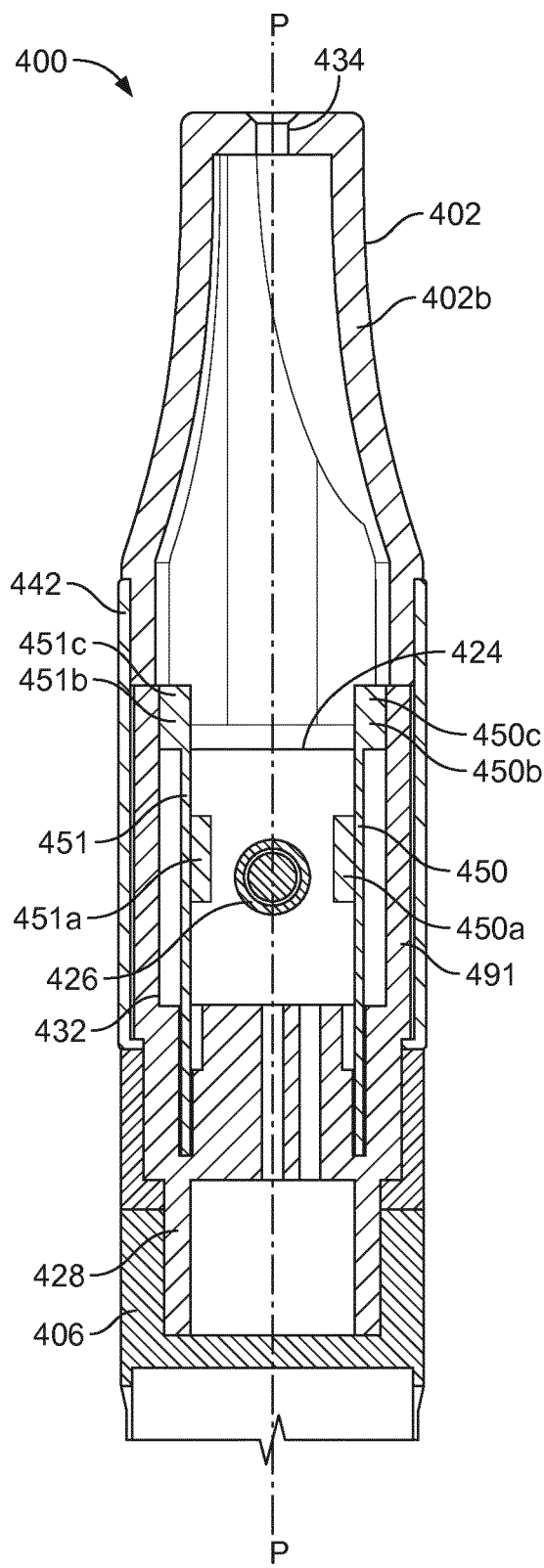
Figure 4D:
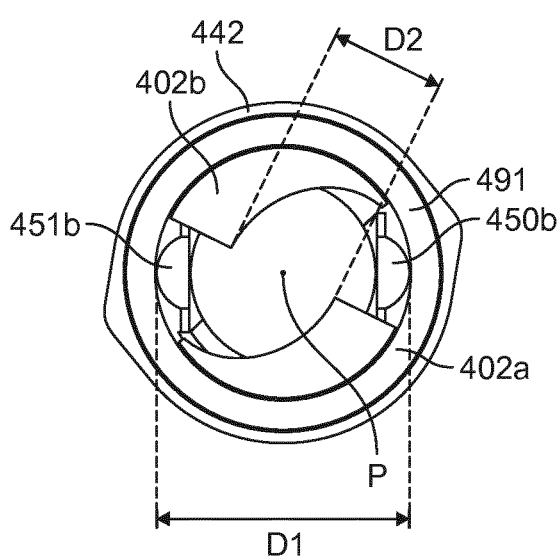
Figure 4E:
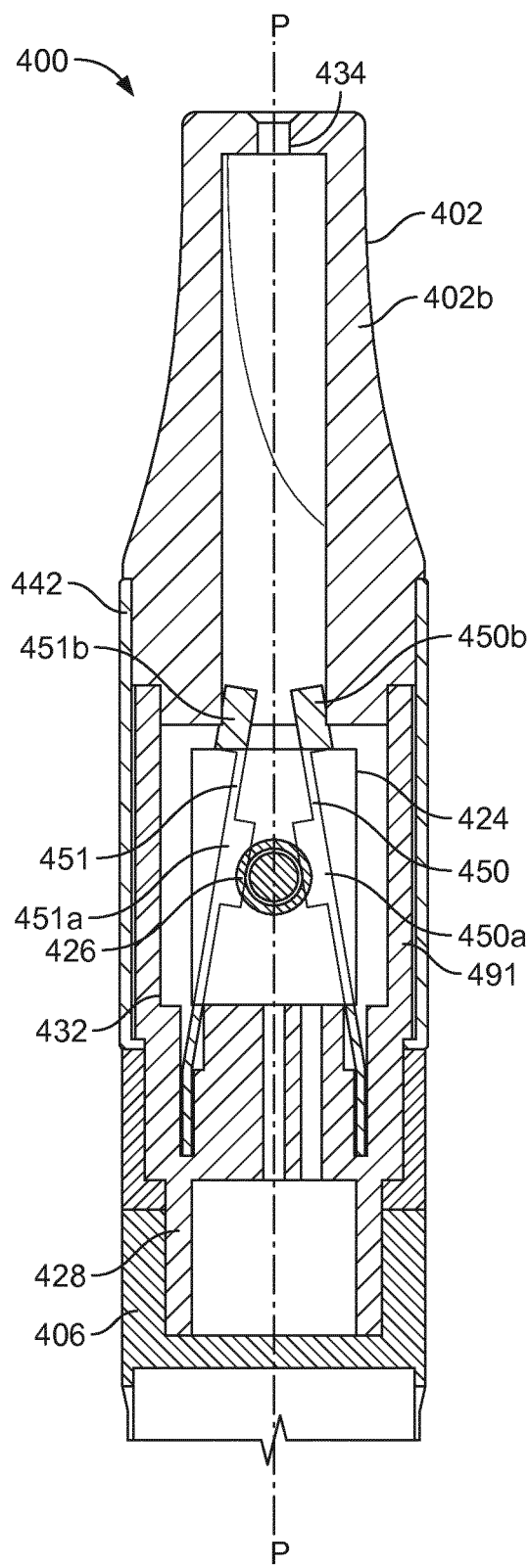
Figure 4F:
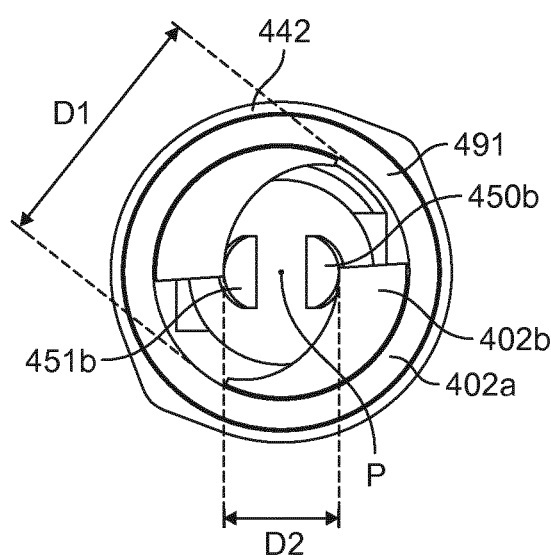

As in the mouth-end section 302 illustrated in FIGS. 3a to 3c, the mouth-end section 402 illustrated in FIGS. 4a to 4f comprises a first portion 402a and a second portion 402b moveable relative to the first portion 402b between a first position (see FIGS. 4a, 4c, 4d) and a second position (see FIGS. 4b, 4e, 4f). Again, the second portion defines an outlet 434 for a user to inhale aerosol from an overall device 400 via the channel 432, and the first portion comprises a connecting means 428 for releasably connecting the mouth-end section 402 to a body 406 of the overall device 400. Again, the first portion 402a comprises resilient members 450, 451 extending along a portion of a channel 432 of the mouth-end section 402 into which a breakable flavor element 424 is received. The resilient members 450, 451 are bendable into the channel 432 from a first element position (see FIGS. 4c, 4d) in which they are substantially parallel with a longitudinal axis P-P of the mouth-end section 402, and a second element position (see FIGS. 4e, 4f) in which they are bent into the channel 432, thereby to break the breakable flavor element 424 received therein.

The resilient members 450, 451 each comprise a respective inward protruding portion 450a, 451a protruding radially inwards towards the channel 432 for contacting and breaking a breakable flavor element 424 received there between. The resilient members 450, 451 each comprise at respective distal ends 450c, 451c an outward protruding portion 450b, 451b protruding out from the channel 432, and for contacting an inner surface of a side wall 491 of the first portion 402b.

However, in this example, rather than being slidable with respect to the first portion 402a substantially parallel to a longitudinal axis P-P of the mouth-end section 402, the second portion 402b is rotatable with respect to the first portion 402a about the longitudinal axis P-P of the receptacle section between the first position (see FIGS. 4a, 4c, 4d) and a second position (see FIGS. 4b, 4e, 4f).

A section of the second portion 402b is received in the first portion 402a. When the second portion is in a first position (see FIGS. 4a, 4c, 4d), an opening 444 in a side wall 442 of the first portion 402a is aligned with an opening 443 in a side wall 491 of the second portion 402b to allow insertion and/or removal of a breakable flavor element 424 into and/or from the channel 432, through the opening 444 of the first portion 402a and the opening 443 of the second portion 402b. When the second portion 402b is in the second position (see FIGS. 4b, 4e, 4f), the opening 444 of the first portion 402a and the opening 443 of the second portion 402b are misaligned such that the side wall 491 of the second portion 402b closes off the opening 444 of the first portion 402a.

The respective distal ends 450c, 451c of the resilient members 450, 451 are received in the second portion 402b. The second portion 402b defines a first inner radial dimension D1 and a second, smaller inner radial dimension D2 (best seen in FIGS. 4d and 4f). The second portion 402b is operable by a user to rotate relative to the first portion 402a about the longitudinal axis P-P of the mouth-end section 402 between a first position (orientation) (see FIGS. 4a, 4c, 4d) and a second position (orientation) (see FIGS. 4b, 4e, 4f).

In the first position (see FIGS. 4c and 4d) the first inner radial dimension D1 is rotationally aligned with the resilient members 450, 451. In this position (orientation), the resilient members 450, 451 experience the larger inner radial dimension D1 of the second portion 402b. The inner radial dimension is approximately the same as or larger than the distance between the outward protruding portions 450b, 451b of the respective resilient members 450, 451 when substantially parallel to the longitudinal axis P-P of the mouth-end section 402, and so the second portion 402b does not displace (bend) the resilient members 450, 451 into the channel 432. The resilient members 450, 451 therefore remain in the first element position (see FIGS. 4c and 4d).

In the second position (orientation) (see FIGS. 4e and 4f) the second inner radial dimension D2 is rotationally aligned with the resilient members 450, 451. In this second position (orientation), the resilient members 450, 451 experience the smaller inner radial dimension D2 of the second portion 402b. The second inner radial dimension D2 is smaller than the distance between the outward protruding portions 450b, 451b of the resilient members 450, 451 when substantially parallel to the longitudinal axis P-P of the mouth-end section 402, and so the second portion 402b displaces (bends) the resilient members 450, 451 inwardly towards the breakable flavor element 424. The resilient members 450, 451 are thereby forced to the second element position (see FIGS. 4e and 4f). Rotation of the second portion 402b relative to the first portion 402a about the longitudinal axis P-P of the mouth-end section 402, from the first portion (see FIGS. 4a, 4c, 4d) to the second position (see FIGS. 4b, 4e, 4f) thereby causes bending of the resilient members 450, 451 from the first element position to the second element position, thereby breaking said breakable flavor element 424 received in the channel 432.

In the example illustrated, the first radial dimension D1 is oriented approximately 140° about the longitudinal axis P-P of the mouth-end section 402 with respect to the second radial dimension D2. In this case, in order to change from the first position to the second position, a user rotates the second portion 402b approximately 140° about the longitudinal axis P-P of the mouth-end section 402.

As best seen in FIGS. 4d and 4f, the inner radial dimension of the second portion 402b varies gradually from the first inner radial dimension D1 to the second inner radial dimension D2. That is, there is not a step change in the inner radial dimension of second portion 402b, but rather a gradual (smooth) increase from small to large at successive points around the circumference of the second portion 402b. This gradual increase effects a 'gearing' that provides a reduction in the degree to which the resilient members 450, 451 are bent for a given degree of rotation of the second portion 402b about the longitudinal axis P-P. This 'gearing' can reduce the torque required to be exerted on the second portion 402b to break the breakable flavor element 424, and hence provides for easy and convenient breaking of a breakable flavor element 424 on installation.

Referring to the sequence illustrated in FIGS. 4a to 4f, in FIGS. 4a, 4c, and 4e, the second portion 402b is the first position, and hence a user may insert a breakable flavor element 424 into the channel 432 through the opening 444 of the first portion 402a and the opening 443 of the second portion 402b. The resilient members 451, 450 are in the first element position, i.e. parallel (unbent) with respect to the longitudinal axis P-P of the mouth-end section 402. A user may rotate the second portion 402b relative to the first portion 402a about the longitudinal axis P-P of the mouth-end section 402 by 140°. This rotation causes the side wall 491 of the second portion 402b to close off the opening 444 of the first portion 402a, and hence install the breakable flavor element 424 into the mouth-end section 402 (see FIG. 4b). This rotation also causes the inner radial dimension of the second portion 402b experienced by the outward protruding portions 450b, 451b of the resilient members 450, 451 to change from the larger D1 to the smaller D2 inner radial dimension. This causes the resilient members 450, 451 to bend inwards towards each other so as to protrude into the channel 432 and break the breakable flavor element 424, thereby releasing flavor from the breakable flavor capsule 426 (see FIGS. 4e and 4f). The second portion 402b is now in the second position, and the resilient members 450, 451 are in the second element position (see FIGS. 4e and 4f). The mouth-end section 402 is now ready to use.

Figure 5A:
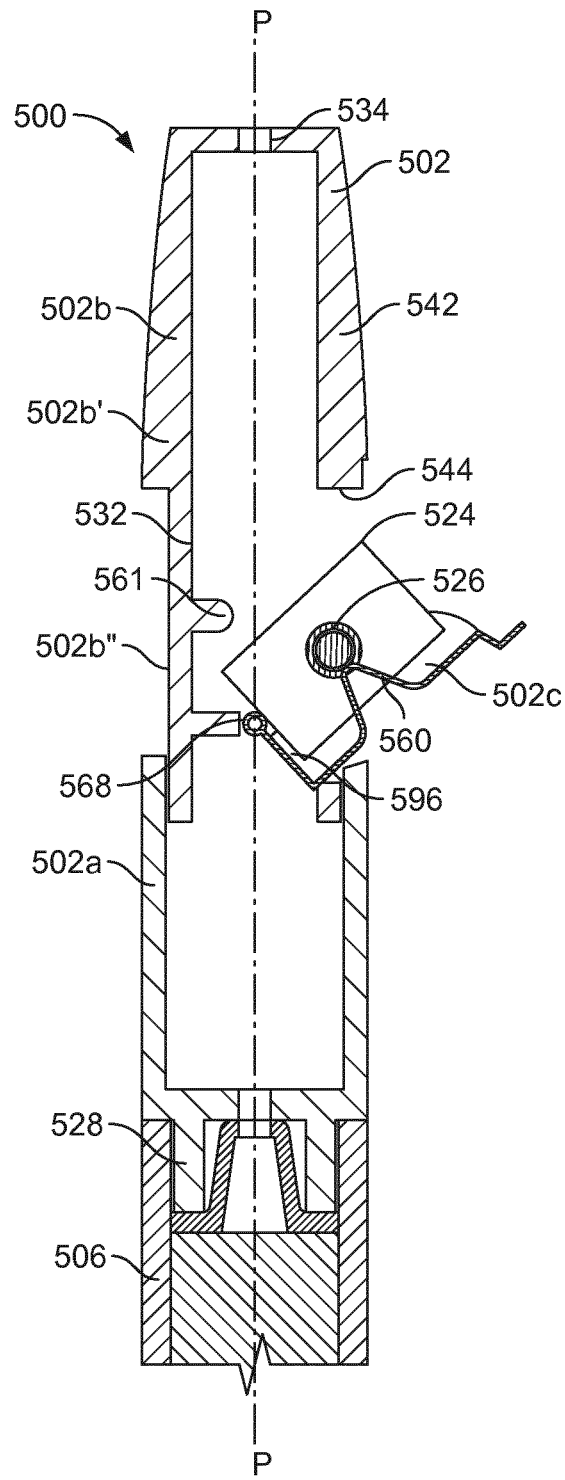
Figure 5B:
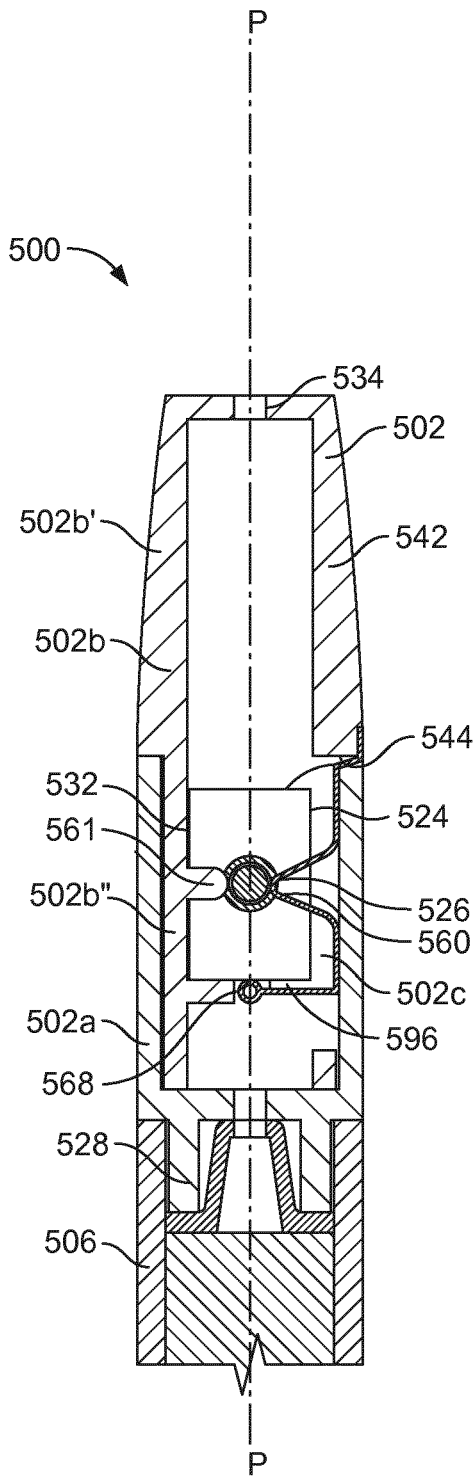

Referring now to FIGS. 5a and 5b, there is illustrated schematically cross sections of another example of a part of a device 500 comprising a receptacle section 502 in different configurations. The example receptacle section 502 in FIGS. 5a and 5b can be used, for example as illustrated in the FIGS. 5a and 5b as the mouth-end section 502 of the device 500, or as some other section of the overall device 500, for example, intermediate of the body 506 of the device 500 and the mouthpiece of the device 300. For brevity, features in FIGS. 5a and 5b and the functioning thereof that are the same or similar to those features already described with reference to FIGS. 4a to 4f are given similar reference numerals to as in FIGS. 4a to 4f but increased by 100, and will not be described in detail again.

As in the mouth-end section 202 illustrated in FIGS. 2a to 2f, the mouth-end section 502 illustrated in FIGS. 5a and 5b comprises a first portion 502a and a second portion 502b slidably mounted within and moveable relative to the first portion 302b, substantially parallel to a longitudinal axis P-P of the mouth-end section 302, between a first position (see FIG. 5a) and a second position (see FIG. 5b). Again, the first portion 502a and the second portion 502b are generally elongate and are hollow. The first portion 502a extends from the body portion 506 of the device 500 via connecting means 528. The second portion 502b comprises a first part 502b' and a second part 502b" that extends from the first part 502b' and has a slightly narrower diameter than does the first part 502b' and which is slidably received in the first portion 502a. A side wall 542 of the second part 502b" of the second portion 502b defines an opening 544 for insertion and/or removal of the flavor element 524, through the opening 544, into the channel 532 internal of the second portion 502b. When the second portion 502b is in the first position (see FIG. 5a) the opening 544 is exposed out of the first portion 502a, and when the second portion 502b is in the second position (see FIG. 5b), the first part 502b' of the second portion 502b abuts against the first portion 502a, and the second part 502b" (and hence the opening 544) of the second portion 502b is within the first portion 502a.

However, unlike the mouth-end section 202 illustrated in FIGS. 2a to 2f, the mouth-end section 502 illustrated in FIGS. 5a and 5b does not comprises resilient members 250, 251 as described above, but instead comprises a third portion 502c for simultaneously closing off the opening 544 in the side wall 542 of the second portion 592b and breaking a breakable flavor element 524 received in the channel 532. The third portion 502c comprises an inward protruding portion 560 protruding towards the channel 532 for contacting and breaking a breakable flavor element 524 received in the channel 532.

The third portion 502c is pivotally mounted to the second part 502b" of the second portion 502b about an axis 568 substantially perpendicular to the longitudinal axis P-P of the mouth-end section 502. The third portion 502c is generally sheet like, but curved to match the curvature of the side wall 542 of the second part 502b" of the second portion 502b. This helps the third portion 502b to effectively close off the opening 544 in the side wall 542 (which is similarly curved).

The third portion 502c is pivotable between an open position (see FIG. 5a) for allowing insertion of the breakable flavor element 524 into the second portion 502b via the opening 544, and a closed position (see FIG. 5b) for closing off the opening 544 and for breaking, via the inward protruding portion 560, the breakable flavor element 524 received in the second portion 502b in use. Movement of the second portion 502b from the first position (see FIG. 5a) to the second position (see FIG. 5a) causes the third portion 502c to pivot from the open position (FIG. 5a) to the closed position (FIG. 5b).

In the open position (see FIG. 5a) the third portion 502c is exposed out of the first portion 502a allowing the third portion 502c to pivot relative to the second part 502b" of the second portion 502b, and hence expose the opening 544 in the side wall 542 of second part 502b" of the second portion 502a for insertion, removal or replacement of a flavor element 542 there through. When the third portion 502c is in the open position, the flavor element 524 may be placed on a ledge or shelf 596 of the third portion 502c in preparation for closing of the third portion 502c and hence insertion of the breakable flavor element 524 into the channel 532.

In the closed position (see FIG. 5b) the third portion 502c covers the opening 544. When the third portion 502c is in the closed position, the inward protruding portion 560 protrudes into the channel 532 thereby to contact and break the breakable flavor element 524 received therein. The second portion 502b comprises an inward protruding portion 561 protruding into the channel 532 from the side wall 542 of the second portion 502b. The inward protruding portion 561 of the second portion 502b is located on an opposite side of the channel to the opening 544. Therefore, when the third portion 502c is in the closed position (see FIG. 5b), the breakable flavor element 524 received in the channel 532 is broken (crushed) between the inward protruding portion 526 of the third portion 502c and the inward protruding portion 561 of the second portion 502b.

The mouth-end section 502 may comprise a biasing means (not shown) to bias the third portion 502c to pivot out and away from second part 502b" of the first portion 502b. In this case, when the second portion 502b is in the first position (see FIG. 5a), the third portion 570 will automatically pivot so as to expose the opening 544 in the side wall 542 of the second part 502b" of the second portion 502b. This allows convenient insertion, removal, or replacement of a flavor element 524 into the channel 532 of the mouth-end section 502.

Referring to the sequence illustrated in FIGS. 5a and 5b, the second portion 502b is initially slid out and away from the first portion 502a, thereby to expose the second part 502b" of the second portion 502b and the third portion 570. The third portion 502c is in the open position so that the opening 544 in the side wall 542 is exposed. It should be noted that the pivoting of the third portion 502c to the open position may occur under gravity, or by manipulation by a user, under the force of a biasing means (not shown) biasing the third portion 502c away from the second part 502b" of the second portion 502b, or by any combination of these. A user may place a flavor element 524 onto the shelf 596 of the third portion 570 (see FIG. 5a).

A user 540 may then push or otherwise manipulate the first part 502b' of the second portion 502b towards the first portion 502a, thereby causing the second part 502b" of the second portion 502b to slide substantially parallel to the longitudinal axis P-P of the mouth-end section 502 into the second position (see FIG. 5b). In so doing, the side wall of the first portion 502a pushes against (urges) the third portion 502c so as to cause the third portion 507 to pivot to the closed position. In doing so the breakable flavor element 524 is broken (crushed) between the inward protruding portion 526 of the third portion 502a and the inward protruding portion 561 of the second portion 502b. Also, the third portion 502c becomes flush with the side wall 542 of the second portion 502b, and thereby closes off the opening 544 (see FIG. 5b). Alternatively a user may manually push the third portion 502c flush with the side wall 542 of the second portion 502b prior to or while pushing the second portion 502b towards the first portion 502a. Once the second portion 502b is pushed so that the side wall 542 and the third portion 502c are fully received in the first portion 502b, the second portion 592b is in the second position, and the mouth-end section 502 is ready to use.

The mouth-end section 502 may comprise a retaining element (not shown) that retains the second portion 502b relative to the first portion 502a so that the second portion 502b is retained in the second position unless a significant force (i.e. the force of a user manually pulling on the second portion 502b) is provided.

Figure 6A:
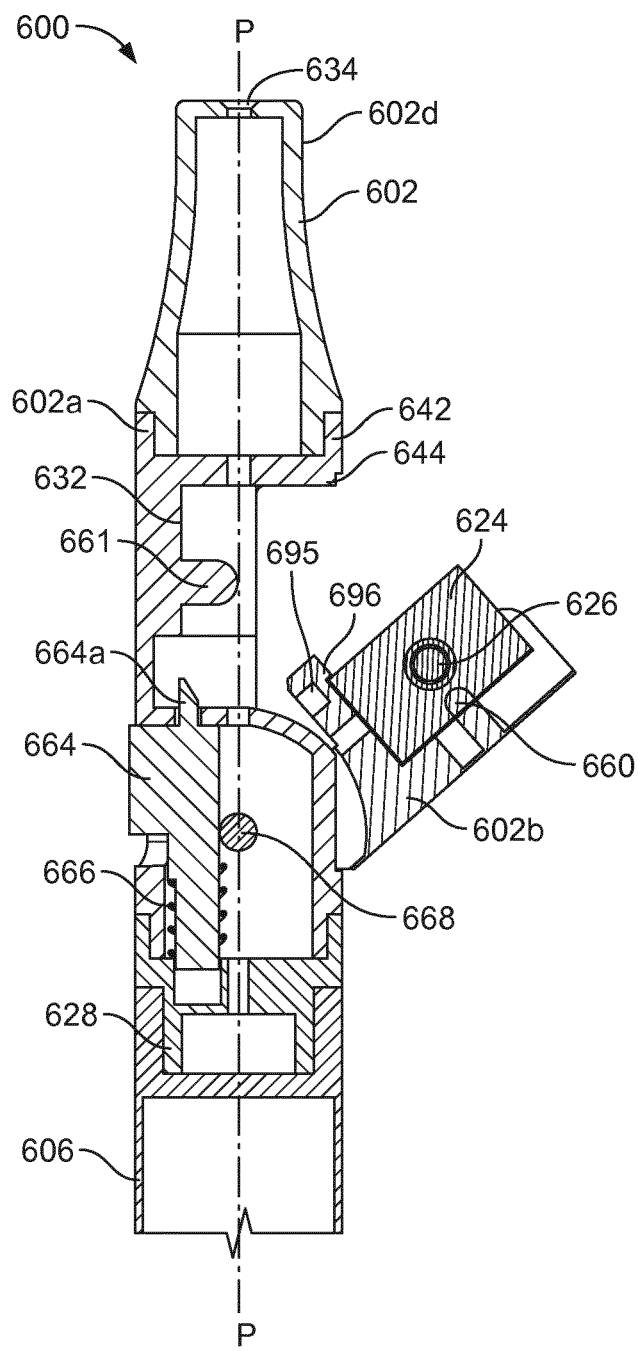
Figure 6B:
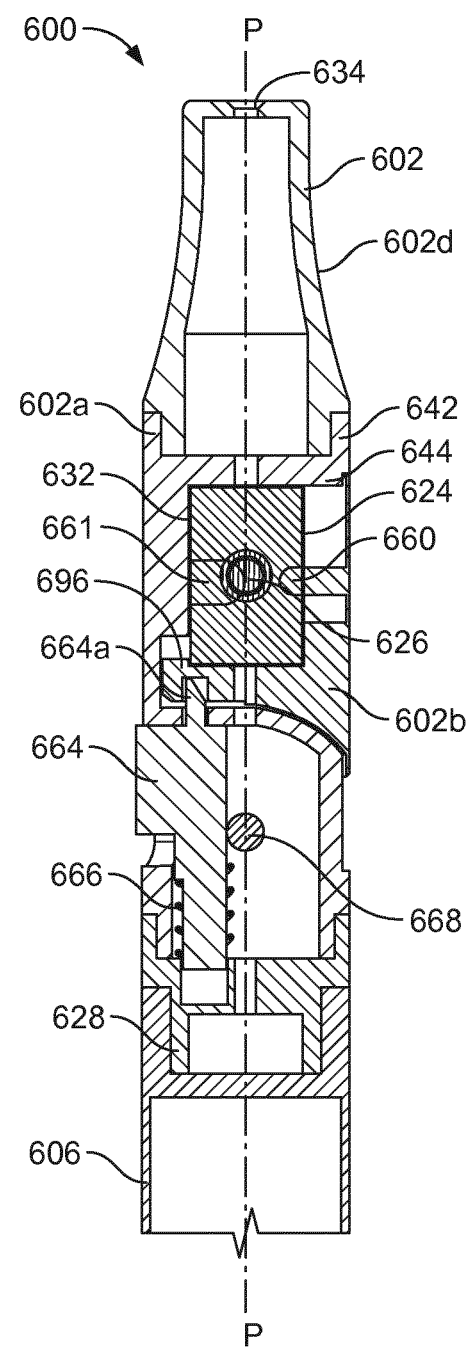

Referring now to FIGS. 6a and 6b, there is illustrated schematically cross sections of a part of an aerosol provision article 600 with another example receptacle section 602 in different configurations. In this example, the receptacle section 602 is again a mouth-end section 602. For brevity, features in FIGS. 6a and 6b and the functioning thereof that are the same or similar to those features already described with reference to FIGS. 5a and 5b are given similar reference numerals to as in FIGS. 5a and 5b but increased by 100, and will not be described in detail again.

As in the mouth-end section 502 illustrated in FIGS. 5a and 5b, the mouth-end section 602 illustrated in FIGS. 6a and 6b comprises a first portion 602a and a second portion 602b moveable relative to the first portion 602a between a first position (see FIG. 6a) for allowing a breakable flavor element 624 to be inserted into a channel 632 internal of the mouth-end section 602, and a second position (see FIG. 6b) for breaking and installing the breakable flavor element 624 into the mouth-end section. The first portion 602a comprises a connecting element 628 for releasably connecting the mouth-end section 602 to a body 606 of the overall device 600.

In this example, however, the movement of the second portion 602b relative to the first portion 602a comprises rotation about an axis 668 substantially perpendicular to the longitudinal axis P-P of the mouth-end section 602. Specifically, the second portion 602b is pivotally mounted 668 to the first portion 602a, thereby to allow pivoting of the second portion 602a relative to the first portion 602a, about an axis 668 substantially perpendicular to the longitudinal axis P-P of the mouth-end section 602, between the first position (FIG. 6a) and the second position (FIG. 6b). The second portion 602b comprises an inward protruding portion 660 protruding towards the channel 632 and is for contacting and breaking a breakable flavor element 524 received in the channel 632.

A mouth portion 602d is for receipt in a user's mouth and defines an outlet 634 for a user to inhale aerosol from the mouth-end section 602 via the channel 632. The mouth portion 602d may be connected to the first portion 602a, for example snap-fitted, or the mouth portion 602d and the first portion 602a may be a single integral part.

A side wall 642 of the first portion 602a defines an opening 644 allowing insertion and/or removal of the flavor element 624 into and/or from a channel 632 internal of the first portion 602a through the opening 644. The first portion 602a is generally cylindrical, and the second portion 602b is generally curved to match the curvature of the side wall 642 of the first portion 602a at the opening 644.

When the second portion 602b is in the first position (FIG. 6a) the second portion 602b is pivoted out and away from the first portion 602a, thereby exposing the opening 644 of the first portion 602a. The pivoting of the second portion 602b out and away from the first portion 602a may be restricted to within a range of angles. For example, the pivoting may be restricted (for example by a stop (not shown)) such that the angle that a plane of the second portion 602b makes with respect the longitudinal axis P-P of the device 600 is restricted to between 0° and 90°, such as between 0° and 45°.

When the second portion 602b is in the second position (FIG. 6b), the second portion 602b is pivoted towards the first portion 602a so as to close off the opening 624. An outer surface of the second portion 602b is flush with an outer surface of the side wall 642 of the first portion 602a. The second portion 602b being generally curved to match the curvature of the side wall 642 of the first portion 1202a at the opening 644 helps the second portion 602b to effectively close off the opening 644. When the second portion 602b is in the second position (FIG. 6b), the inward protruding portion 660 protrudes into the channel 632 through the opening 644 thereby to contact and break the breakable flavor element 624 received therein. The second portion 602b comprises an inward protruding portion 661 protruding into the channel 632 from the side wall 642 of the second portion 602b. The inward protruding portion 661 of the second portion 602b is located on an opposite side of the channel 632 to the opening 644. Therefore, when the second portion 502b is in the second position (see FIG. 6b), the breakable flavor element 624 received in the channel 632 is broken (crushed) between the inward protruding portion 660 of the second portion 602b and the inward protruding portion 661 of the first portion 602a.

The second portion 602b comprises a protrusion or shelf 696 that extends out at or near a right angle to the plane of the second portion 602b. The shelf 696 is for supporting a breakable flavor element 624 in the second portion 602b. This can be useful, for example, to support the flavor element 624 in the second portion 602b when the second portion is in the first position (FIG. 6a).

The first portion 602a comprises a retaining element 664 to releasably retain the second portion 602b in the second position (FIG. 6b). Specifically, the retaining element 664 comprises a protrusion or latch 664a. The latch 664a is releasably receivable in a recess or notch 695 in the shelf 696 of the second portion 602b. When the second portion 602b is in the second position, the latch 664a is received in the notch 695 thereby to retain or latch the second portion 60b in the second position. The mouth-end section 602 comprises a biasing means, such as a spring 666, to bias the retaining element 664 for receipt of the latch 664a in the notch 695. The latch 664a is operable by a user (not shown), against the spring 666, to release the latch 664a from the notch 695, thereby to release the second portion 602b to be able to pivot to the first position.

Referring to the sequence illustrated in FIGS. 6a and 6b, a user (not shown) manually operates the retaining element 664 to release the second portion 602b from the first portion 602a. The second portion 602b then pivots about the axis 668, for example by 45°, out and away from the first portion 602a, under gravity, by manipulation by a user, by a biasing means (not shown) for biasing the second portion 602b to pivot out and away from the first portion 602a, or any combination of these (not shown). A user then places a breakable flavor element 624 into the second portion 602b so as to rest on the shelf 696 of the second portion 602b (FIG. 6a). A user then pushes or otherwise manipulates the second portion 602b so that the second portion 602b pivots about the axis 668 towards the first portion 602a. In doing so, the flavor element 624 is inserted through the opening 644 of the side wall 642 of the first portion 602a, and the second portion 602b closes off the opening 644. Also, in doing so, the breakable flavor element 624 received in the channel 632 is broken (crushed) between the inward protruding portion 660 of the second portion 602b and the inward protruding portion 661 of the first portion 502a. As the second portion 602b is pivoted towards the closed position, the latch 664a of the retaining element 664 of the first portion 602a engages with (protrudes into) the notch 695 of the second portion 602b, and thereby retains the second portion 602b relative to the first portion 602a. The second portion 602b is thereby in the second position (FIG. 6b), and the breakable flavor element 624 is thereby both broken and installed into the mouth-end section 602. The mouth-end section 602 is thereby ready to use.

Although in the examples described above the various receptacle sections 102, 202, 302, are generally described as being arranged to break a breakable flavor element 124, 224, 324 etc. by crushing a flavor capsule 126, 226, 326 etc., it will be appreciated that there are other ways in which a flavor element 124, 224, 324 etc. may be broken. For example, alternatively or in addition, the receptacle sections 102, 202, 302 may break a flavor element 124, 224, 324 etc. by piercing, puncturing, cutting, or slicing a flavor capsule 126, 226, 326 etc. of a flavor element 124, 224, 324 etc. For example, breaking elements (such as for example resilient members 250, 251, 350, 351, etc. or inwardly protruding portions 560, 660 etc.) may comprise a spike or other sharp protrusion for piercing or puncturing a flavor capsule 126, 226, 326, or an edge for cutting or slicing a flavor capsule 126, 226, 326 etc. of a flavor element 124, 224, 324 etc. for example.

Although in the examples described above the various receptacle sections 102, 202, 302, are described as being arranged to break a breakable flavor element 124, 224, 324 etc. on installation of the breakable flavor element 124, 224, 324 etc. into the receptacle section, this is not essential, and the various receptacle sections 102, 202, 302 may be arranged to activate any suitable activatable element 124, 224, 324 etc. by applying a force to activate the activatable element 124, 224, 324 etc. on installation of the activatable element 124, 224, 324 etc. into the receptacle section 102, 202, 302 etc. In other words, rather than the receptacle section being arranged to break, on installation of a breakable flavor element in the receptacle section by a user, the breakable flavor element, the receptacle section may be arranged to apply, on installation of an activatable element in the receptacle section by a user, a force to the activatable flavor element to activate the activatable element.

In some examples, the activatable element may comprise a reservoir of flavorant (for example in the form of a liquid and/or gel). The reservoir may be wrapped or embedded in a suitable carrier material, such as cellulose acetate. The reservoir may have resilient or deformable walls. The reservoir may have an aperture allowing flavorant to be released from the reservoir to the carrier material. When a force is applied to the activatable element by a receptacle section as described in detail in any one of the various above examples (for example via activating element(s) such as for example resilient members 250, 251, 350, 351, etc. or inwardly protruding portions 560, 660 etc.), the reservoir is squeezed (deformed) and the flavorant is thereby forced from the reservoir through the aperture into the carrier material. The receptacle section thereby activates an activatable flavor element by applying a force, on installation of the activatable flavor element into the receptacle section, to the activatable element.

In some examples, the activatable element may comprise flavor material, for example solid material, that which when ground, exposed, or otherwise suitably physically activated, releases a flavorant. The flavor material may be, for example, ground tobacco. The flavor material may be for example wrapped partially or wholly in a wrapper, and/or the flavor material may be supported in a resilient housing, for example a plastic housing, or may be held or embedded in a suitable carrier material such as cellulose acetate. When a force is applied to the activatable element by a receptacle section as described in detail in any one of the various above examples (for example via resilient members 250, 251, 350, 351, etc. or via inward protruding portions 560, 660 etc. as described above), the solid material is exposed or otherwise suitably physically activated, and a flavorant (or an increase and/or change in flavorant) is released thereby to impart a flavor (or increased and/or different flavor) to the aerosol flow. The receptacle section thereby activates an activatable flavor element by applying a force, on installation of the activatable flavor element into the receptacle section, to the activatable element.

Although in the examples described above, the activatable element 124, 224, 324 etc. received in the various receptacle sections 202, 302, 402 etc. is a flavor element 124, 224, 324 etc. and is for imparting a flavor to the aerosol when the aerosol flows through the flavor element 124, 224, 324 etc., this is not essential and instead (or in addition) the element 124, 224, 324 etc. may be for modifying a property of the aerosol other than (or in addition) to flavor, for example comprise a substance for modifying a property of the aerosol other than (or in addition) to flavor.

In some examples, the element 124, 224, 324 etc. may comprise a substance that modifies one or more other organoleptic properties of the aerosol (e.g. modifying the feel or smell or look of the aerosol to the user).

In some examples, the element 124, 224, 324 etc. may comprise a substance that modifies the PH of the aerosol by either lowering or raising the PH (e.g. modifying the acidity or the basicity of the aerosol).

In some examples, the element 124, 224, 324 etc. may comprise a substance that modifies (e.g. reduce) the amount of aldehydes in the aerosol.

In some examples, the element 124, 324, 324 etc. may comprise a substance that modifies different combinations of two or more of these or indeed other properties of the aerosol.

Although in the above described examples, the device 100, 200, 300 etc. generates the aerosol by heating a liquid (the device is of type commonly referred to as an e-cig), this is not essential and in other examples, the device may generate the aerosol by heating, but not burning (combusting), a material, for example comprising a solid material, that may contain for example tobacco (e.g. a device sometimes referred to as a Tobacco Heating Product (THP) device).

In the above examples, the liquid container 122 was cylindrical in shape and defined a cylindrical channel 104 running through the length of the liquid container 122. However, in other examples, the liquid container may not be annular in shape, and/or the liquid container may comprise an outer shell that defines an annular channel between the liquid container and the outer shell through which vapor or aerosol may also, or instead, pass.

Indeed, it will be readily appreciated that there are many configurations of aerosol provision articles such as so called e-cigarette devices (some of which not having refillable liquid containers integral to the device as such, but rather, for example, replaceable cartridges, for example comprising integral atomizers, i.e. so called "cartomizers") and that the above examples may also be applied to these or other configurations or to other aerosol provision articles.

In the above examples, reference was made to the mouth-end sections having two resilient members, or two protruding portions, or the like. It will be readily appreciated however that in other examples the various mouth-end sections may have only one such resilient member or protruding portion, or in yet other examples may have more than two, for example, 3, 4, 5 6 . . . N, resilient members and/or protruding portions. In yet other examples, the various resilient members and/or protruding portions may extend continuously around the circumference or a portion of the circumference of a channel into which a breakable flavor element is received, for example so as to be generally annular in shape, or have the form of a portion of an annulus.

As used herein, the terms "flavor" and "flavorant" may refer to materials which, where local regulations permit, may be used to create a desired taste or aroma in a product for adult consumers. They may include extracts (e.g., licorice, hydrangea, Japanese white bark magnolia leaf, chamomile, fenugreek, clove, menthol, Japanese mint, aniseed, cinnamon, herb, wintergreen, cherry, berry, peach, apple, Drambuie, bourbon, scotch, whiskey, spearmint, peppermint, lavender, cardamom, celery, cascarilla, nutmeg, sandalwood, bergamot, geranium, honey essence, rose oil, vanilla, lemon oil, orange oil, cassia, caraway, cognac, jasmine, ylang-ylang, sage, fennel, piment, ginger, anise, coriander, coffee, or a mint oil from any species of the genus Mentha), flavor enhancers, bitterness receptor site blockers, sensorial receptor site activators or stimulators, sugars and/or sugar substitutes (e.g., sucralose, acesulfame potassium, aspartame, saccharine, cyclamates, lactose, sucrose, glucose, fructose, sorbitol, or mannitol), and other additives such as charcoal, chlorophyll, minerals, botanicals, or breath freshening agents. They may be imitation, synthetic or natural ingredients or blends thereof. They may be in any suitable form, for example, oil, liquid, solid, or powder. For example, a liquid, oil, or other such fluid flavorant may be impregnated in a porous solid material so as to impart flavor and/or other properties to that porous solid material. As such, the liquid or oil is a constituent of the material in which it is impregnated.

The above embodiments are to be understood as illustrative examples of the invention. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

The invention claimed is:

1. A receptacle section for an aerosol provision article, the aerosol provision article for generating a flow of aerosol in use, the receptacle section comprising:
    a receptacle section arranged for having installed therein an activatable element for modifying, once activated, a property of the flow of aerosol, the receptacle section being arranged to apply, on installation of the activatable element in the receptacle by a user, a force to the activatable element to activate the activatable element
    wherein the receptacle section comprises a first portion and a second portion, the second portion being moveable relative to the first portion between a first position and a different, second position, wherein movement of the second portion from the first position to the second position causes the force to be applied to activate the activatable element when the activatable element is installed in the receptacle,
    wherein the receptacle section comprises at least one activating element operable to move between a first element position and a different, second element position, wherein movement of the second portion from the first position to the second position causes the at least one activating element to move from the first element position to the second element position, and wherein movement of the activating element from the first element position to the second element position causes the force to be applied to the activatable element installable in the receptacle section, and
    wherein the receptacle section defines a channel for receiving the activatable element, wherein the at least one activating element comprises a resilient member extending along at least a portion of the channel, and wherein the resilient member is operable to bend between the first element position and the second element position, wherein in the second element position at least a portion of the resilient member protrudes into the channel, thereby to apply the force to activate the activatable element received in the channel in use.

2. The receptacle section according to claim 1, wherein either:
    the first position is for allowing insertion of the activatable element in the receptacle by a user, or
    when the second portion is in the second position the receptacle section defines a flow path for the aerosol to flow through the receptacle section via the activatable element installed in the receptacle in use.

3. The receptacle section according to claim 1, wherein either:
    the resilient member comprises an inward protruding portion protruding from the resilient member towards the channel, the inward protruding portion being for contacting the activatable element received in the channel in use, thereby to apply the force to activate the activatable flavour element received in the channel in use, or
    the receptacle section comprises at least two resilient members, a first resilient member being located on an opposite side of the channel to a second resilient member.

4. The receptacle section according to claim 1, wherein one of the first portion or the second portion comprises the resilient member, the resilient member being receivable in the other of the first portion or the second portion, the resilient member comprising an outward protruding portion, the outward protruding portion protruding out from the resilient member away from the channel and for contacting an inner wall of the other of the first portion or the second portion, wherein the movement of the second portion from the first position to the second position causes the outward protruding portion to contact the other of the first portion or the second portion, thereby to bend the resilient member from the first element position to the second element position.

5. The receptacle section according to claim 4, wherein the inner wall of the other of the first portion or the second portion comprises an inward protruding portion protruding out of the inner wall towards the resilient member, for contacting the outward protruding portion of the resilient member.

6. The receptacle section according to claim 4, wherein the second portion is slidably mounted to the first portion thereby to allow sliding of the second portion relative to the first portion, parallel to a longitudinal axis of the receptacle section, between the first position and the second position.

7. The receptacle section according to claim 6, wherein the second portion is receivable in the first portion, and a side wall of the second portion defines an opening, wherein when the second portion is in the first position, the opening is exposed for insertion or removal of the activatable element into the channel through the opening, and wherein when the second portion is in the second position, the opening is closed off by the first portion.

8. The receptacle section according to claim 4, wherein the second portion is removable from the first portion.

9. The receptacle section according to claim 1, wherein second portion is rotatable with respect to the first portion about a longitudinal axis of the receptacle section, the second portion defining a first inner radial dimension and a second, smaller inner radial dimension, the second portion being operable by a user to rotate between the first position and the second position, wherein in the first position the first inner radial dimension is rotationally aligned with the resilient member, and in the second position the second inner radial dimension is rotationally aligned with the resilient member, wherein rotation of the second portion from the first position to the second position causes the resilient member to bend from the first element position to the second element position, thereby to apply the force to activate the activatable element received in the channel in use.

10. The receptacle section according to claim 9, wherein either:

the inner radial dimension of the second portion varies gradually from the first inner radial dimension to the second inner radial dimension, or the second portion is received in the first portion, and when the second portion is in the first portion, an opening in a side wall of the first portion is aligned with an opening in a side wall of the second portion to allow insertion or removal of the activatable element into or from the channel, through the opening of the first portion and the opening of the second portion, and wherein when the second portion is in the second position, the opening of the first portion and the opening of the second portion are misaligned such that a side wall of the second portion closes off the opening of the first portion.

11. The receptacle section according to claim 1, wherein the second portion is slidable in the first portion, between the first position and the second position, substantially parallel to a longitudinal axis of the receptacle section, and the receptacle section comprises a third portion for closing off an opening in a side wall of the second portion, the third portion comprising an inward protruding portion for contacting and applying the force to activate the breakable flavour element received in the second portion, the third portion being pivotally mounted to the second portion about an axis substantially perpendicular to the longitudinal axis of the receptacle section, thereby allowing pivoting of the third portion between an open position for allowing insertion of the activatable element into the second portion via the opening, and a closed position for closing off the opening and for applying the force, via the inward protruding portion, to activate the activatable element received in the second portion in use.

12. The receptacle section according to claim 11, wherein movement of the second portion from the first position to the second position causes the third portion to pivot from the open position to the closed position.

13. The receptacle section according to claim 1, wherein the second portion is pivotally mounted to the first portion, thereby to allow pivoting of the second portion relative to the first portion, about an axis substantially perpendicular to a longitudinal axis of the receptacle section, between the first position and the second position.

14. The receptacle section according to claim 13, wherein the second portion comprises an inward protruding portion for applying the force to the activatable element, wherein a side wall of the first portion defines an opening allowing, when the second portion is in the first position, insertion or removal of the activatable element into or from the receptacle, through the opening, and wherein when the second portion is pivoted to the second position the second portion closes off the opening and the inward protruding portion applies the force to activate the activatable element.

15. The receptacle section according to claim 1, wherein the activatable element is installed in the receptacle.

16. The receptacle section according to claim 15, wherein the activatable element comprises a substance for modifying the property of the aerosol, and the force causes the substance to be exposed, thereby to modify the property of the flow of aerosol.

17. The receptacle according to claim 1, wherein the property is one or more of an organoleptic property of the aerosol, a flavor of the aerosol, or a pH of the aerosol.

18. A mouthpiece for an aerosol provision article, the aerosol provision article being for generating a flow of aerosol in use, the mouthpiece comprising the receptacle section of claim 1.

19. An aerosol provision article for generating a flow of aerosol in use, the aerosol provision article comprising the receptacle section of claim 1.

20. The aerosol provision article according to claim 19, further comprising:

a container for holding a liquid or a material; and a heater for volatilizing liquid held in the container to generate the flow of aerosol in use or for heating without combusting the material to generate the flow of aerosol in use.

* * * * *